(12) United States Patent
Jerri et al.

(10) Patent No.: US 10,900,002 B2
(45) Date of Patent: Jan. 26, 2021

(54) MICROCAPSULES WITH HIGH DEPOSITION ON SURFACES

(71) Applicant: Firmenich SA, Satigny (CH)

(72) Inventors: Huda Jerri, Plainsboro, NJ (US); Valery Normand, Plainsboro, NJ (US); Christopher Hansen, Plainsboro, NJ (US)

(73) Assignee: Firmenich SA, Satigny (CH)

( * ) Notice: Subject to any disclaimer, the term of this patent is extended or adjusted under 35 U.S.C. 154(b) by 64 days.

(21) Appl. No.: 15/574,265

(22) PCT Filed: Jun. 3, 2016

(86) PCT No.: PCT/EP2016/062660
§ 371 (c)(1),
(2) Date: Nov. 15, 2017

(87) PCT Pub. No.: WO2016/193435
PCT Pub. Date: Dec. 8, 2016

(65) Prior Publication Data
US 2018/0078468 A1 Mar. 22, 2018

Related U.S. Application Data

(60) Provisional application No. 62/171,723, filed on Jun. 5, 2015.

(30) Foreign Application Priority Data

Jun. 24, 2015 (EP) .................................. 15173503

(51) Int. Cl.

| | | |
|---|---|---|
| *C11D 9/00* | (2006.01) | |
| *A61K 8/11* | (2006.01) | |
| *A61Q 13/00* | (2006.01) | |
| *A61K 8/73* | (2006.01) | |
| *A61K 8/81* | (2006.01) | |
| *A61K 8/65* | (2006.01) | |
| *A61K 8/84* | (2006.01) | |
| *A61K 8/87* | (2006.01) | |
| *A61Q 1/00* | (2006.01) | |

(52) U.S. Cl.
CPC .................. *C11D 9/00* (2013.01); *A61K 8/11* (2013.01); *A61K 8/65* (2013.01); *A61K 8/73* (2013.01); *A61K 8/8158* (2013.01); *A61K 8/84* (2013.01); *A61K 8/87* (2013.01); *A61Q 1/00* (2013.01); *A61Q 13/00* (2013.01); *A61K 2800/5424* (2013.01); *A61K 2800/5426* (2013.01); *A61K 2800/5428* (2013.01); *A61K 2800/56* (2013.01); *A61K 2800/624* (2013.01); *A61K 2800/652* (2013.01)

(58) Field of Classification Search
None
See application file for complete search history.

(56) References Cited

U.S. PATENT DOCUMENTS

| | | |
|---|---|---|
| 5,538,751 A | 7/1996 | Carter et al. |
| 7,417,021 B2 | 8/2008 | Calias et al. |
| 2005/0112152 A1 | 5/2005 | Popplewell et al. |
| 2006/0216509 A1 | 9/2006 | Kleban et al. |

FOREIGN PATENT DOCUMENTS

| | | |
|---|---|---|
| WO | 2001041915 A1 | 6/2001 |
| WO | 0197851 A2 | 12/2001 |
| WO | 0228889 A2 | 4/2002 |
| WO | 2009153695 A1 | 12/2009 |
| WO | 2010092176 A2 | 8/2010 |
| WO | 2011056904 A1 | 5/2011 |
| WO | 2014044840 A1 | 3/2014 |
| WO | 2015023961 A1 | 2/2015 |

OTHER PUBLICATIONS

International Search Report for application No. PCT/EP2016/062660 dated Jul. 22, 2016.

*Primary Examiner* — Robert A Wax
*Assistant Examiner* — Randeep Singh
(74) *Attorney, Agent, or Firm* — Armstrong Teasdale LLP

(57) ABSTRACT

The present invention relates to microcapsules formed by interfacial polymerization, which present high deposition properties and which can be advantageously used for example in the perfumery industry. Perfuming compositions and perfumed consumer products comprising these microcapsules are also objects of the invention.

12 Claims, 7 Drawing Sheets

FIGURES

Capsule B　　　　　Capsule F　　　　　Capsule G

MICROCAPSULES WITH HIGH DEPOSITION ON SURFACES

RELATED APPLICATIONS

This application is a national stage application under 35 U.S.C. § 371 filing of International Patent Application PCT/EP2016/062660, filed Jun. 3, 2016, which claims the benefit of U.S. Provisional Application No. 62/171,723, filed Jun. 5, 2015 and European patent application no 15173503.2 filed Jun. 24, 2015. The contents of which are incorporated herein by reference in their entirety.

TECHNICAL FIELD

The present invention relates to the field of delivery systems. More specifically, the invention concerns microcapsules formed by interfacial polymerization, which have a particularly high rate of deposition when applied on a substrate and which can be advantageously used in several industries, in particular in the perfumery industry. Perfuming compositions and perfumed consumer products comprising these microcapsules are also objects of the invention.

The microcapsules comprise an anionic or amphiphilic biopolymer and a cationic polymer in specific relative proportions.

BACKGROUND OF THE INVENTION

One of the problems faced by the perfumery industry lies in the relatively rapid loss of the olfactive benefit provided by odoriferous compounds due to their volatility, particularly that of "top-notes". This problem is generally tackled using a delivery system, e.g. capsules containing a perfume, to release the fragrance in a controlled manner.

In order to be successfully used in consumer products, perfume delivery systems must meet a certain number of criteria. The first requirement concerns stability in aggressive medium. In fact delivery systems may suffer from stability problems, in particular when incorporated into surfactant-based products such as detergents, wherein said systems tend to degrade and lose efficiency in the perfume-retention ability. It is also difficult to have a good stability and a good dispersion of the capsules altogether. The dispersion factor is very important because the aggregation of capsules increases the tendency of the capsule-containing product to phase separate, which represents an real disadvantage. On the other hand, perfume delivery systems must also perform during the actual use of the end-product by the consumer, in particular in terms of odor performance, as the perfume needs to be released when required. Another issue faced for example by the perfumery industry is to provide delivery systems that are well deposited on the substrate for the treatment of which the end product is intended to be used, such as textile, skin, hair or other surfaces, so as to possibly remain on the substrate even after a rinsing step. To address this specific problem, the use of cationic capsules has been described in the prior art. Cationic capsules are also known to be better dispersed in several applications.

For example, WO 01/41915 discloses a process for the preparation of capsules carrying cationic charges. Such a process is allegedly applicable to a large variety of microcapsules, in particular polyurethane-polyurea microcapsules are mentioned. After their formation, the capsules are placed in a medium which is favourable for the treatment with cationic polymers. The treatment with cationic polymers is carried out after purification of the basic capsule slurry, in order to eliminate anionic or neutral polymers which were not incorporated in the capsule wall during formation thereof, and other free electrically charged compounds involved in the encapsulation process. In particular, the capsules are diluted, isolated and then re-suspended in water, or even washed to further eliminate anionic compounds. After the purification step, the capsules are agitated vigorously and the cationic polymers are added. Partially quaternized copolymers of polyvinylpyrrolidones are cited to this purpose, among many other suitable polymers. The described process comprises several steps following the capsule formation, said process being therefore time consuming and not economically profitable.

US 2006/0216509 also discloses a process to render polyurea capsules positively-charged. This process involves the addition, during the wall formation, of polyamines, the capsules thus bearing latent charges, depending on the pH of the medium. Once formed, the capsules are subsequently cationized by acid action or alkylation to bear permanent positive charges. The cationic compounds therefore react with the capsule wall, chemically changing the latter.

WO2009/153695 from the applicant discloses a simplified process for the preparation of polyurea microcapsules bearing permanent positive charges based on the use of a specific stabilizer and which present good deposition on a substrate.

Despite those prior disclosures, there is still a need to improve the ability of perfume delivery systems to deposit on a substrate and to adhere on the substrate for leave-on and rinse-off applications, while performing in terms of perfume release and stability.

The microcapsules of the invention solve this problem as they proved to show huge improvement in terms of deposition properties compared to what was known heretofore such as cationic delivery systems.

The present invention provides new microcapsules for delivering an encapsulated perfume and/or other hydrophobic materials, which combine the presence of a biopolymer and a cationic polymer in specific ratios. None of the above-cited prior art documents teaches such a combination.

SUMMARY OF THE INVENTION

The present invention solves the above-mentioned problems by providing microcapsules with boosted deposition properties. In particular the association of cationic deposition-promoting aids with an emulsifier consisting of an anionic or amphiphilic biopolymer in particular ratios is unexpectedly tremendously improving the percentage of deposition of microcapsules on a substrate.

A first object of the invention is therefore a core-shell microcapsule slurry comprising at least one microcapsule having
  a) an oil-based core;
  b) a polymeric shell formed by interfacial polymerisation in the presence of an amphiphilic or anionic biopolymer; and
  c) a coating comprising a cationic polymer;
wherein the weight ratio between said biopolymer and the cationic polymer in the slurry is comprised between 0.2 and 20.

A second object of the invention is a microcapsule powder obtained by drying the slurry as defined in the present invention.

A third object of the invention is a process for the preparation of microcapsules slurry or microcapsule powder, comprising the following steps:

a) Dissolving at least one polyisocyanate having at least two isocyanate groups in an oil to form an oil phase;
b) Preparing an aqueous solution of an anionic or amphiphilic biopolymer to form a water phase;
c) Adding the oil phase to the water phase to form an oil-in-water dispersion, wherein the mean droplet size is comprised between 1 and 500 µm, preferably between 5 and 50 µm;
d) Applying conditions sufficient to induce interfacial polymerisation and form microcapsules in form of a slurry;
e) Adding a cationic polymer; and
f) Optionally drying the capsule slurry to obtain microcapsule powder;

wherein the biopolymer and the cationic polymer are added in amounts such that the weight ratio between the biopolymer and the cationic polymer in the slurry is comprised between 0.2 and 20.

A fourth object of the invention is a perfuming composition comprising the microcapsule slurry or the microcapsule powder as defined above, wherein the core comprises a perfume.

A fifth object of the invention is a consumer product comprising the microcapsule slurry or the microcapsule powder or a perfuming composition as defined above.

A sixth object of the invention is a method for improving deposition of microcapsules on a surface, which comprises treating said surface with a perfuming composition or a consumer product as defined above.

DETAILED DESCRIPTION OF THE INVENTION

Figure 1:
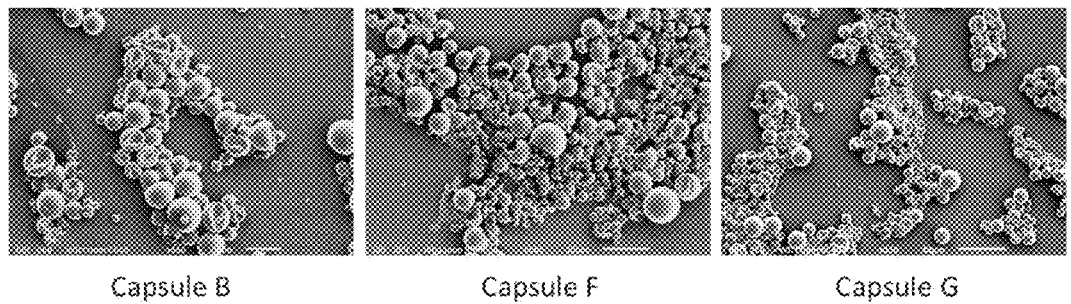
FIG. 1: microscopic pictures of microcapsules according to the invention, synthesized using different biopolymer, namely Gum Arabic (Capsule B), Sodium Caseinate (Capsule F) and Soy Protein (Capsule G).

Unless stated otherwise, percentages (%) are meant to designate a percentage by weight of a composition.

By "biopolymers" it is meant biomacromolecules produced by living organisms. Biopolymers are characterized by molecular weight distributions ranging from 1,000 (1 thousand) to 1,000,000,000 (1 billion) Daltons. These macromolecules may be carbohydrates (sugar based) or proteins (amino-acid based) or a combination of both (gums) and can be linear or branched.

According to the invention, the biopolymers have not been modified by means of chemical derivatization to chemically graft on different functional groups with different properties. As an example, carboxymethylcellulose (CMC) is not a biopolymer according to the invention.

In the context of this invention, the biomacromolecules or biopolymers are preferentially surface active materials and should be amphiphilic or anionic namely negatively charged in water at a pH greater than 9.

By "quaternized polymer" it is meant here that the cationic polymer is positively charged. The quaternized polymer or polyquaternium designation indicates the presence of quaternary ammonium cation functionalities in the polymer which render the polymer positively charged.

By "polyurea-based" wall or shell, it is meant that the polymer comprises urea linkages produced by either an amino-functional crosslinker or hydrolysis of isocyanate groups to produce amino groups capable of further reacting with isocyanate groups during interfacial polymerization.

By "polyurethane-based" wall or shell, it is meant that the polymer contains urethane linkages produced by reaction with polyols.

By "oil", it is meant an organic phase that is liquid at about 20° C. which forms the core of the core-shell capsules. According to any one of the invention embodiments, said oil comprises an ingredient or composition selected amongst a perfume, flavour, cosmetic ingredient, insecticide, malodour counteracting substance, bactericide, fungicide, insect repellent or attractant, drug, agrochemical ingredient and mixtures thereof.

By "perfume or flavour oil" also referred to as "perfume or flavour", it is meant a single perfuming or flavouring compound or a mixture of several perfuming or flavouring compounds.

For the sake of clarity, by the expression "dispersion" in the present invention it is meant a system in which particles are dispersed in a continuous phase of a different composition and it specifically includes a suspension or an emulsion.

It has been found that the known effect of cationic polymer as a deposition aid for delivery systems could be significantly and unexpectedly enhanced when such cationic polymer was associated with the use of an anionic or amphiphilic biopolymer in specific respective ratios.

A first object of the present invention therefore consists of a core-shell microcapsule slurry comprising at least one microcapsule having
  a) an oil-based core;
  b) a polymeric shell formed by interfacial polymerisation in the presence of an anionic or amphiphilic biopolymer; and
  c) a coating comprising a cationic polymer; wherein the weight ratio between the biopolymer and the cationic polymer in the slurry is comprised between 0.2 and 20.

Preferably the weight ratio between the biopolymer and the cationic polymer in the slurry is comprised between 0.25 and 5, more preferably between 0.5 and 2.0.

According to a particular embodiment, the coating consists of a cationic polymer.

The anionic or amphiphilic biopolymer is preferably chosen from the group consisting of gum Arabic, soy protein, gelatin (type A and type B), sodium caseinate, bovine serum albumin, sugar beet pectin, hydrolyzed soy protein, hydrolyzed sericin, Pseudocollagen, Biopolymer SA-N, Pentacare-NA PF, a mixture of gum Arabic and Revitalin and mixtures thereof.

Suitable gum Arabic includes in particular Acacia Senegal, Acacia Seyal and mixtures thereof.

According to a particular embodiment, the biopolymer comprises sodium caseinate.

According to another embodiment, the biopolymer comprises gum Arabic.

According to another embodiment, the biopolymer comprises gelatin.

According to another embodiment, the biopolymer comprises soy protein.

According to another embodiment, the biopolymer comprises bovine serum albumin.

According to another embodiment, the biopolymer comprises sugar beet pectin.

According to another embodiment, the biopolymer comprises hydrolyzed soy protein.

According to another embodiment, the biopolymer comprises Purolan Sericin (INCI Name: hydrolyzed sericin; origin Lanxess).

According to another embodiment, the biopolymer comprises Pseudocollagen (INCI Name: Yeast Extract; origin Lonza).

According to another embodiment, the biopolymer comprises Biopolymer SA-N (INCI Name: Hyaluronic Acid (and) Albumen (and) Dextran Sulfate; origin Lipo Chemicals).

According to another embodiment, the biopolymer comprises Pentacare-NA PF PF (INCI Name: Hydrolyzed Wheat Gluten (and) *Ceratonia Siliqua* (Carob) Gum (and) Aqua (and) Sodium Dextran Sulfate (and) Bis-Hydroxyethyl Tromethamine (and) Phenoxyethanol (and) Ethylhexylglycerin; origin DSM Nutritional Products, LLC).

According to a particular embodiment, the biopolymer is a mixture comprising gum Arabic and Revitalin (INCI Name: Glycoproteins (and) Glutamic Acid (and) Valine (and) Threonine (and) Aqua (and) Phenoxyethanol (and) Ethylhexylglycerin (and) Sodium Metabisulfite; origin DSM Nutritional Products, LLC).

Suitable cationic polymers for the purpose of the invention include quaternized polymers. Preferably the cationic polymer is selected from the group consisting of dimethyl diallyl ammonium chloride homopolymer, copolymer of dimethyl diallyl ammonium chloride with acrylamide, hydroxypropyl trimethyl ammonium chloride ether of hydroxyethyl cellulose, quaternized copolymer of polyvinyl pyrrolidone and dimethylaminoethyl methacrylate, guar hydroxypropyl trimethyl ammonium chloride functionalized polysaccharide, quaternized chitosan, quaternized proteins, collagens and keratins, aminosilicones and mixtures thereof. According to particular embodiment, the quaternized polymer is selected from the group consisting of a cationic acrylic copolymer (INCI Name: acrylamidopropyltrimonium chloride/acrylamide copolymer), a cationic homopolymer of diallyl dimethyl ammonium chloride (INCI Name: Polyquaternium PQ 6), a cationic co-polymer of diallyl dimethyl ammonium chloride and acrylamide (INCI Name: Polyquaternium 7), a cationic hydroxyethyl cellulose (INCI Name: Polyquaternium PQ 10), cationic guar gum, 2-hydroxy-3-(trimethylammonium)propyl ether chloride, Laurdimonium Hydroxypropyl Hydrolysed Collagen, Hydrolysed Wheat Protein PG-Propyl Silanetriol, Vinyl Amine/Vinyl Alcohol Copolymer, or cationic Amino Functional Silicone, PEG-7 Amodimethicone and mixtures thereof.

According to a preferred embodiment, the cationic polymer consists of a cationic acrylic copolymer (INCI Name: acrylamidopropyltrimonium chloride/acrylamide copolymer).

According to a particular embodiment:
  the cationic polymer consists of acrylamidopropyltrimonium chloride/acrylamide copolymer and the anionic biopolymer consists of gum Arabic; or
  the cationic polymer consists of acrylamidopropyltrimonium chloride/acrylamide copolymer and the anionic biopolymer consists of sodium caseinate; or
  the cationic polymer consists of acrylamidopropyltrimonium chloride/acrylamide copolymer and the anionic biopolymer consists of soy protein; or
  the cationic polymer consists of acrylamidopropyltrimonium chloride/acrylamide copolymer and the anionic biopolymer consists of Gelatin type A; or
  the cationic polymer consists of acrylamidopropyltrimonium chloride/acrylamide copolymer and the anionic biopolymer consists of Gelatin type B; or
  the cationic polymer consists of acrylamidopropyltrimonium chloride/acrylamide copolymer and the anionic biopolymer consists of Bovine serum albumine; or
  the cationic polymer consists of acrylamidopropyltrimonium chloride/acrylamide copolymer and the anionic biopolymer consists of sugar beet pectin; or
  the cationic polymer consists of acrylamidopropyltrimonium chloride/acrylamide copolymer and the anionic biopolymer consists of sericin; or
  the cationic polymer consists of acrylamidopropyltrimonium chloride/acrylamide copolymer and the anionic biopolymer consists of pseudocollagen; or the cationic polymer consists of acrylamidopropyltrimonium chloride/acrylamide copolymer and the anionic biopolymer consists of a biopolymer SA-N; or the cationic polymer consists of acrylamidopropyltrimonium chloride/acrylamide copolymer and the anionic biopolymer consists of a pentacare NA-PF; or the cationic polymer consists of acrylamidopropyltrimonium chloride/acrylamide copolymer and the anionic biopolymer consists of a mixture of Revitalin with gum Arabic; or the cationic polymer consists of Polyquaternium PQ6 and the anionic biopolymer consists of gum Arabic; or the cationic polymer consists of Polyquaternium PQ10 and the anionic biopolymer consists of gum Arabic; or the cationic polymer consists of Cassia Hydroxypropyltrimonium Chloride Polymer and the anionic biopolymer consists of gum Arabic; or the cationic polymer consists of Hydrolysed Wheat Protein PG-Propyl Silanetriol and the anionic biopolymer consists of gum Arabic; or the cationic polymer consists of PEG-7 Amodimethicone and the anionic biopolymer consists of gum Arabic; or the cationic polymer consists of Vinyl Amine/Vinyl Alcohol Copolymer and the anionic biopolymer consists of gum Arabic; or the cationic polymer consists of Laurdimonium Hydroxypropyl Hydrolysed Collagen and the anionic biopolymer consists of gum Arabic; or the cationic polymer consists of Guar Hydroxypropyltrimonium Chloride and the anionic biopolymer consists of gum Arabic.

According to a particular embodiment, the oil-based core comprises a perfume or flavour. According to a preferred embodiment, the oil-based core comprises a perfume.

The perfume or flavour can be a perfuming or flavouring ingredient alone or a mixture of ingredients, in the form of a perfuming or flavouring composition. Specific examples of such perfuming and flavouring ingredients may be found in the current literature, for example in Perfume and Flavour Chemicals, 1969 (and later editions), by S. Arctander, Montclair N.J. (USA), as well as in the vast patent and other literature related to the perfume and flavour industry. They are well known to the skilled person in the art of perfuming or flavouring consumer products, that is, of imparting or modulating odour or taste to a consumer product.

In case of a perfume, the perfuming ingredients may be dissolved in a solvent of current use in the perfume industry. The solvent is preferably not an alcohol. Examples of such solvents are diethyl phthalate, isopropyl myristate, Abalyn®, benzyl benzoate, ethyl citrate, limonene or other terpenes, or isoparaffins. Preferably, the solvent is very hydrophobic and highly sterically hindered, like for example Abalyn®. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

Preferred perfuming ingredients are those having a high steric hindrance and in particular those from one of the following groups:

Group 1: perfuming ingredients comprising a cyclohexane, cyclohexene, cyclohexanone or cyclohexenone ring substituted with at least one linear or branched $C_1$ to $C_4$ alkyl or alkenyl substituent;

Group 2: perfuming ingredients comprising a cyclopentane, cyclopentene, cyclopentanone or cyclopentenone ring substituted with at least one linear or branched $C_4$ to $C_8$ alkyl or alkenyl substituent;

Group 3: perfuming ingredients comprising a phenyl ring or perfuming ingredients comprising a cyclohexane, cyclohexene, cyclohexanone or cyclohexenone ring substituted with at least one linear or branched $C_5$ to $C_8$ alkyl or alkenyl substituent or with at least one phenyl substituent and optionally one or more linear or branched $C_1$ to $C_3$ alkyl or alkenyl substituents;

Group 4: perfuming ingredients comprising at least two fused or linked $C_5$ and/or $C_6$ rings;

Group 5: perfuming ingredients comprising a camphor-like ring structure;

Group 6: perfuming ingredients comprising at least one C7 to C20 ring structure;

Group 7: perfuming ingredients having a log P value above 3.5 and comprising at least one tert-butyl or at least one trichloromethyl substitutent; Examples of ingredients from each of these groups are:

Group 1: 2,4-dimethyl-3-cyclohexene-1-carbaldehyde (origin: Firmenich SA, Geneva, Switzerland), isocyclocitral, menthone, isomenthone, Romascone® (methyl 2,2-dimethyl-6-methylene-1-cyclohexanecarboxylate, origin: Firmenich SA, Geneva, Switzerland), nerone, terpineol, dihydroterpineol, terpenyl acetate, dihydroterpenyl acetate, dipentene, eucalyptol, hexylate, rose oxide, Perycorolle® ((S)-1,8-p-menthadiene-7-ol, origin: Firmenich SA, Geneva, Switzerland), 1-p-menthene-4-ol, (1RS,3RS,4SR)-3-p-mentanyl acetate, (1R,2S,4R)-4,6,6-trimethyl-bicyclo[3,1,1]heptan-2-ol, Doremox® (tetrahydro-4-methyl-2-phenyl-2H-pyran, origin: Firmenich SA, Geneva, Switzerland), cyclohexyl acetate, cyclanol acetate, Fructalate® (1,4-cyclohexane diethyldicarboxylate, origin: Firmenich SA, Geneva, Switzerland), Koumalactone® ((3ARS,6SR,7ASR)-perhydro-3,6-dimethyl-benzo[B]furan-2-one, origin: Firmenich SA, Geneva, Switzerland), Natactone® ((6R)-perhydro-3,6-dimethyl-benzo[B]furan-2-one, origin: Firmenich SA, Geneva, Switzerland), 2,4,6-trimethyl-4-phenyl-1,3-dioxane, 2,4,6-trimethyl-3-cyclohexene-1-carbaldehyde;

Group 2: (E)-3-methyl-5-(2,2,3-trimethyl-3-cyclopenten-1-yl)-4-penten-2-ol (origin: Givaudan SA, Vernier, Switzerland), (1'R,E)-2-ethyl-4-(2',2',3'-trimethyl-3'-cyclopenten-1'-yl)-2-buten-1-ol (origin: Firmenich SA, Geneva, Switzerland), Polysantol® ((1'R,E)-3,3-dimethyl-5-(2',2',3'-trimethyl-3'-cyclopenten-1'-yl)-4-penten-2-ol, origin: Firmenich SA, Geneva, Switzerland), fleuramone, Hedione® HC (methyl-cis-3-oxo-2-pentyl-1-cyclopentane acetate, origin: Firmenich SA, Geneva, Switzerland), Veloutone® (2,2,5-Trimethyl-5-pentyl-1-cyclopentanone, origin: Firmenich SA, Geneva, Switzerland), Nirvanol® (3,3-dimethyl-5-(2,2,3-trimethyl-3-cyclopenten-1-yl)-4-penten-2-ol, origin: Firmenich SA, Geneva, Switzerland), 3-methyl-5-(2,2,3-trimethyl-3-cyclopenten-1-yl)-2-pentanol (origin, Givaudan SA, Vernier, Switzerland);

Group 3: damascones, Neobutenone® (1-(5,5-dimethyl-1-cyclohexen-1-yl)-4-penten-1-one, origin: Firmenich SA, Geneva, Switzerland), nectalactone ((1'R)-2-[2-(4'-methyl-3'-cyclohexen-1'-yl)propyl]cyclopentanone), alpha-ionone, beta-ionone, damascenone, Dynascone® (mixture of 1-(5,5-dimethyl-1-cyclohexen-1-yl)-4-penten-1-one and 1-(3,3-dimethyl-1-cyclohexen-1-yl)-4-penten-1-one, origin: Firmenich SA, Geneva, Switzerland), Dorinone® beta (1-(2,6,6-trimethyl-1-cyclohexen-1-yl)-2-buten-1-one, origin: Firmenich SA, Geneva, Switzerland), Romandolide® ((1S,1'R)-[1-(3',3'-Dimethyl-1'-cyclohexyl)ethoxycarbonyl]methyl propanoate, origin: Firmenich SA, Geneva, Switzerland), 2-tert-butyl-1-cyclohexyl acetate (origin: International Flavors and Fragrances, USA), Limbanol® (1-(2,2,3,6-tetramethyl-cyclohexyl)-3-hexanol, origin: Firmenich SA, Geneva, Switzerland), trans-1-(2,2,6-trimethyl-1-cyclohexyl)-3-hexanol (origin: Firmenich SA, Geneva, Switzerland), (E)-3-methyl-4-(2,6,6-trimethyl-2-cyclohexen-1-yl)-3-buten-2-one, terpenyl isobutyrate, Lorysia® (4-(1,1-dimethylethyl)-1-cyclohexyl acetate, origin: Firmenich SA, Geneva, Switzerland), 8-methoxy-1-p-menthene, Helvetolide® ((1S,1'R)-2-[1-(3',3'-dimethyl-1'-cyclohexyl) ethoxy]-2-methylpropyl propanoate, origin: Firmenich SA, Geneva, Switzerland), para tert-butylcyclohexanone, menthenethiol, 1-methyl-4-(4-methyl-3-pentenyl)-3-cyclohexene-1-carbaldehyde, allyl cyclohexylpropionate, cyclohexyl salicylate, 2-methoxy-4-methylphenyl methyl carbonate, ethyl 2-methoxy-4-methylphenyl carbonate, 4-ethyl-2-methoxyphenyl methyl carbonate;

Group 4: Methyl cedryl ketone (origin: International Flavors and Fragrances, USA), Verdylate, vetyverol, vetyverone, 1-(octahydro-2,3,8,8-tetramethyl-2-naphtalenyl)-1-ethanone (origin: International Flavors and Fragrances, USA), (5RS,9RS,10SR)-2,6,9,10-tetramethyl-1-oxaspiro[4.5]deca-3,6-diene and the (5RS,9SR,10RS) isomer, 6-ethyl-2,10,10-trimethyl-1-oxaspiro[4.5]deca-3,6-diene, 1,2,3,5,6,7-hexahydro-1,1,2,3,3-pentamethyl-4-indenone (origin: International Flavors and Fragrances, USA), Hivernal® (a mixture of 3-(3,3-dimethyl-5-indanyl)propanal and 3-(1,1-dimethyl-5-indanyl)propanal, origin: Firmenich SA, Geneva, Switzerland), Rhubofix® (3',4-dimethyl-tricyclo[6.2.1.0(2,7)]undec-4-ene-9-spiro-2'-oxirane, origin: Firmenich SA, Geneva, Switzerland), 9/10-ethyldiene-3-oxatricyclo[6.2.1.0(2,7)]undecane, Polywood® (perhydro-5,5,8A-trimethyl-2-naphthalenyl acetate, origin: Firmenich SA, Geneva, Switzerland), octalynol, Cetalox® (dodecahydro-3a,6,6,9a-tetramethyl-naphtho[2,1-b]furan, origin: Firmenich SA, Geneva, Switzerland), tricyclo[5.2.1.0(2,6)]dec-3-en-8-yl acetate and tricyclo[5.2.1.0(2,6)]dec-4-en-8-yl acetate as well as tricyclo[5.2.1.0(2,6)]dec-3-en-8-yl propanoate and tricyclo[5.2.1.0(2,6)]dec-4-en-8-yl propanoate, (+)-(1S,2S,3S)-2,6,6-trimethyl-bicyclo[3.1.1]heptane-3-spiro-2'-cyclohexen-4'-one;

Group 5: camphor, borneol, isobornyl acetate, 8-isopropyl-6-methyl-bicyclo[2.2.2]oct-5-ene-2-carbaldehyde, camphopinene, cedramber (8-methoxy-2,6,6,8-tetramethyl-tricyclo[5.3.1.0(1,5)]undecane, origin: Firmenich SA, Geneva, Switzerland), cedrene, cedrenol, cedrol, Florex® (mixture of 9-ethylidene-3-oxatricyclo[6.2.1.0(2,7)]undecan-4-one and 10-ethylidene-3-oxatricyclo[6.2.1.0(2,7)]undecan-4-one, origin: Firmenich SA, Geneva, Switzerland), 3-methoxy-7,7-dimethyl-10-methylene-bicyclo[4.3.1]decane (origin: Firmenich SA, Geneva, Switzerland);

Group 6: Cedroxyde® (trimethyl-13-oxabicyclo-[10.1.0]-trideca-4,8-diene, origin: Firmenich SA, Geneva, Switzerland), Ambrettolide LG ((E)-9-hexadecen-16-olide, origin: Firmenich SA, Geneva, Switzerland), Habanolide® (pentadecenolide, origin: Firmenich SA, Geneva, Switzerland), muscenone (3-methyl-(4/5)-cyclopentadecenone, origin: Firmenich SA, Geneva, Switzerland), muscone (origin: Firmenich SA, Geneva, Switzerland), Exaltolide® (pentadecanolide, origin: Firmenich SA, Geneva, Switzerland), Exaltone® (cyclopentadecanone, origin: Firmenich SA, Geneva, Switzerland), (1-ethoxyethoxy)cyclododecane (origin: Firmenich SA, Geneva, Switzerland), Astrotone, 4,8-cyclodecadien-1-one;

Group 7: Lilial® (origin: Givaudan SA, Vernier, Switzerland), rosinol.

Preferably, the perfume comprises at least 30%, preferably at least 50%, more preferably at least 60% of ingredients selected from Groups 1 to 7, as defined above. More preferably said perfume comprises at least 30%, preferably at least 50% of ingredients from Groups 3 to 7, as defined above. Most preferably said perfume comprises at least 30%, preferably at least 50% of ingredients from Groups 3, 4, 6 or 7, as defined above.

According to another preferred embodiment, the perfume comprises at least 30%, preferably at least 50%, more preferably at least 60% of ingredients having a log P above 3, preferably above 3.5 and even more preferably above 3.75.

Preferably, the perfume used in the invention contains less than 10% of its own weight of primary alcohols, less than 15% of its own weight of secondary alcohols and less than 20% of its own weight of tertiary alcohols. Advantageously, the perfume used in the invention does not contain any primary alcohols and contains less than 15% of secondary and tertiary alcohols.

The polymeric shell of the microcapsule according to the present invention is formed by interfacial polymerization in the presence of the anionic or amphiphilic biopolymer.

According to one embodiment, said shell is polyurea-based. According to another embodiment, the shell is polyurethane-based.

Another object of the invention is a microcapsule powder obtained by drying the slurry as defined above.

Another object of the present invention is a process for the preparation of microcapsule slurry or microcapsule powder as defined above, comprising the following steps:
a) dissolving at least one polyisocyanate having at least two isocyanate groups in an oil to form an oil phase;
b) preparing an aqueous solution of an anionic or amphiphilic biopolymer to form a water phase;
c) adding the oil phase to the water phase to form an oil-in-water dispersion, wherein the mean droplet size is comprised between 1 and 500 um;
d) applying conditions suitable to induce interfacial polymerization and form microcapsules in the form of a slurry;
e) adding a cationic polymer;
f) optionally drying the slurry to obtain microcapsule powder;
wherein the biopolymer and the cationic polymer are added in amounts such that the weight ratio between the biopolymer and the cationic polymer in the slurry is comprised between 0.2 and 20.

The combined use of biopolymer and cationic polymer in claimed proportions in capsules according to the invention significantly improves the deposition promotion compared to what was known in the art. Without being bound by theory, it is believed that the biopolymer used as emulsifier is also providing functional anchoring sites with favorable surface conformations and a high local density of anionic charge groups onto the surface of the microcapsules resulting in improved conjugation of cationic deposition-promoting materials compared to traditionally employed modified or unmodified polyvinyl alcohol colloidal stabilizers.

The process according to the present invention is therefore characterized by the use of an anionic or amphiphilic biopolymer in the preparation of the aqueous phase and acting as an emulsifier, which is used in combination with deposition-promoting material, in particular a cationic polymer in a weight ratio comprised between 0.2 and 20.

The process according to the invention comprises the preparation of an oil phase by dissolving a polyisocyanate having at least two isocyanate groups in an oil. According to any one of the invention embodiments, the oil contains a hydrophobic material selected from the group consisting of a perfume, flavour, cosmetic ingredient, insecticide, malodour counteracting substance, bactericide, fungicide, insect repellent or attractant, drug, agrochemical ingredient and mixtures thereof. According to a particular embodiment, the oil contains a perfume or flavour as defined above.

According to a preferred embodiment of the invention, there is used an amount of between 10 and 60%, more preferably between 20 and 50% of oil in the process of the invention, these percentages being defined by weight relative to the total weight of the obtained microcapsule slurry.

Suitable polyisocyanates used according to the invention include aromatic polyisocyanate, aliphatic polyisocyanate and mixtures thereof. Said polyisocyanate comprises at least 2, preferably at least 3 but may comprise up to 6, or even only 4, isocyanate functional groups. According to a particular embodiment, a triisocyanate (3 isocyanate functional group) is used.

According to one embodiment, said polyisocyanate is an aromatic polyisocyanate. The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets, polyisocyanurates and trimethylol propane adducts of diisocyanates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

According to another embodiment, said polyisocyanate is an aliphatic polyisocyanate. The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

According to another embodiment, the at least one polyisocyanate is in the form of a mixture of at least one aliphatic polyisocyanate and of at least one aromatic polyisocyanate, both comprising at least two or three isocyanate functional groups, such as a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate. Preferably, when used as a mixture the molar ratio between the aliphatic polyisocyanate and the aromatic polyisocyanate is ranging from 80:20 to 10:90.

The at least one polyisocyanate used in the process according to the invention is present in amounts representing from 1 to 15%, preferably from 2 to 8% and more preferably from 2 to 6% by weight of the microcapsule slurry.

The at least one polyisocyanate is dissolved in an oil, which in a particular embodiment contains a perfume or flavour. The oil can contain a further oil-soluble benefit agent to be co-encapsulated with the perfume and flavour with the purpose of delivering additional benefit on top of perfuming or taste-related. As non-limiting examples, ingredients such as cosmetic, skin caring, malodor counteracting, bactericide, fungicide, pharmaceutical or agrochemical ingredient, a diagnostic agent and/or an insect repellent or attractant and mixtures thereof can be used.

According to a particular embodiment, the oil phase further comprises a silane or a combination of silanes to form a hybridized inorganic/organic membrane at the interface based on sol-gel polymerization and interfacial polymerization. According to a particular embodiment tetraethoxysilane (TEOS) is used.

The process according to the present invention includes the use an anionic of amphiphilic biopolymer in the preparation of the aqueous phase. Those materials defined above include in particular proteins and polysaccharides. The biopolymer is preferably comprised in an amount ranging from 0.1 to 5.0% by weight of the microcapsule slurry, preferably between 1 and 2 wt % of the microcapsule slurry.

The capsules according to the present invention have a wall that is formed by interfacial polymerization. A skilled person in the art is well aware of various ways to induce interfacial polymerization.

According to a first embodiment, capsules according to the present invention are polyurea-based capsules. According to a particular embodiment, interfacial polymerization is induced by addition of a polyamine reactant. Preferably, the reactant is selected from the group consisting of water soluble guanidine salts and guanazole to form a polyurea wall with the polyisocyanate. According to another embodiment, polyurea-based capsules are formed in absence of added polyamine reactant, and result only from the autopolymerization of the at least one polyisocyanate, preferably in the presence of a catalyst.

According to a second embodiment, capsules according to the present invention are polyurethane-based capsules. According to this particular embodiment, interfacial polymerization is induced by addition of a polyol reactant. Preferably the reactant is selected from the group consisting of monomeric and polymeric polyols with multiple hydroxyl groups available for reaction and mixtures thereof.

According to a third embodiment, capsules according to the present invention are polyurea/polyurethane based. In that case interfacial polymerization is induced by addition of a mixture of the reactant mentioned under precedent first and second embodiments.

Additionally, crosslinkers with both amino groups and hydroxyl groups can be used to generate polyurea/polyurethane materials. Furthermore, polyisocyanates with both urea and urethane functionalities can be used to generate polyurea/polyurethane materials.

According to a fourth embodiment, capsules according to the present invention are organic-inorganic hybrid capsules.

According to this particular embodiment, an orthosilicate, a silane or a combination of silanes can be added from the oil phase or the water phase to form a hybridized inorganic/organic membrane or surface coating. Silanes can be suspended in the oil phase to silicify the inner membrane, or can be added post-emulsification to form a silicified shell around the burgeoning polymeric capsule membrane. Inside-out and outside-in sol gel polymerization can occur by forming and hardening 3D siloxane bonds inside or outside the polymer membrane via condensation of alkoxide in or on the emulsion droplets.

Process conditions for interfacial polymerization do not need further description here as they are well known to a skilled person in the art.

The process according to the invention comprises the addition of a cationic polymer. Said polymer can be added any time after forming the dispersion. It can for example be added to the capsule slurry before or after crosslinking, when the capsule slurry is heated, or after it has cooled. The slurry conditions and pH can be optimized according to standard practice by a skilled person in the art. Suitable cationic polymers are mentioned above. The cationic polymer is preferably present in an amount comprised between 0.1 to 5% by weight of the microcapsule slurry, more preferably between 0.5 and 2% by weight of the microcapsule slurry.

According to a particular embodiment of the invention, the microcapsule slurry can be submitted to a drying, like spray-drying, to provide the microcapsules as such, i.e. in a powder form. It is understood that any standard method known by a person skilled in the art to perform such drying is applicable. In particular the slurry may be spray-dried preferably in the presence of a polymeric carrier material such as polyvinyl acetate, polyvinyl alcohol, dextrins, natural or modified starch, vegetable gums such as gum arabic, pectins, xanthans, alginates, carrageenans or cellulose derivatives to provide microcapsules in a powder form. Preferably, the carrier is a gum Arabic. According to one embodiment, the biopolymer used as emulsified is also used as carrier material for further drying and the emulsifier or carrier also has the capacity to further encapsulate free perfume oil in addition to the microcapsules. According to a particular embodiment, the carrier material contains free perfume oil which can be same or different from the perfume from the core of the microcapsules.

The biopolymer used as an emulsifier during the interfacial polymerisation and formation of the microcapsules is surprisingly significantly boosting the effect of the deposition promoting polymer. Therefore when microcapsules are applied on a substrate, the percentage of deposition is much higher than that of known systems as shown in the examples below. Consequently, the olfactive performance measured through fragrance intensity during use in application, is tremendously improved. A method for improving deposition of microcapsules on a surface including but not limited to fabric, skin and hair, comprising treating said surface with a perfuming composition or a perfumed article comprising microcapsules as defined above is therefore also an object of the invention. Preferably the treated surface is hair or skin.

A further object of the present invention is a perfuming composition comprising
(i) microcapsule slurry or microcapsule powder as defined above, wherein the oil comprises a perfume; and
(ii) at least one ingredient selected from the group consisting of a perfumery carrier and a perfuming co-ingredient.
(iii) optionally a perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect or modulate the overall odour and which is not a microcapsule as defined above. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.1 and 30% by weight of microcapsule slurry or microcapsule powder as defined above.

The invention's microcapsules can advantageously be used in all the fields of modern perfumery, i.e. fine or functional perfumery. Consequently, another object of the present invention is represented by a perfuming consumer product comprising as a perfuming ingredient, the microcapsules defined above or a perfuming composition as defined above.

The invention's microcapsules can therefore be added as such or as part of an invention's perfuming composition in a perfuming consumer product.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises a functional formulation, as well as optionally additional benefit agents, corresponding to the desired consumer product, e.g. a detergent or an air freshener, and an olfactive effective amount of at least one invention's compound.

The nature and type of the constituents of the perfumery consumer product do not warrant a more detailed description here, which in any case would not be exhaustive, the skilled person being able to select them on the basis of his general knowledge and according to the nature and the desired effect of said product. Formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

In particular, examples of such formulations can be found in handbooks such as for example Handbook of detergents; CTFA Cosmetic ingredient handbook, $10^{th}$ edition or more recent versions; Formulating detergents and personal care products: a guide to product development (2000); Cosmetic formulation of skin care products (2006) as well as in the abundant patent literature in the field of body care and home care consumer products.

Non-limiting examples of suitable perfumery consumer product include a perfume, such as a fine perfume, a cologne or an after-shave lotion; a fabric care product, such as a liquid or solid detergent, tablets and pods, a fabric softener, a dryer sheet, a fabric refresher, an ironing water, or a bleach; a body-care product, such as a hair care product (e.g. a shampoo, leave-on or rinse-off hair conditioner, styling product, dry shampoo, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, shave gel or foam, cleansing wipes or a hygiene product); an air care product, such as an air freshener or a "ready to use" powdered air freshener; or a home care product, such all-purpose cleaners, liquid or power or tablet dishwashing products, toilet cleaners or products for cleaning various surfaces, for example sprays & wipes intended for the treatment/refreshment of textiles or hard surfaces (floors, tiles, stone-floors etc.). According to a preferred embodiment, the consumer product is a shampoo or a rinse-off conditioner. According to another preferred embodiment, the product is a perfumed soap. According to another preferred embodiment, the product is a body wash.

Preferably, the consumer product comprises from 0.1 to 15 wt %, more preferably between 0.2 and 5 wt % of the microcapsule slurry or microcapsule powder of the present invention, these percentages being defined by weight relative to the total weight of the consumer product. Of course the above concentrations may be adapted according to the olfactive effect desired in each product.

The capsules of the invention have proven to be particularly useful in rinse-off application as their deposition is much superior to delivery systems known heretofore.

The invention will now be further described by way of examples. It will be appreciated that the invention as claimed is not intended to be limited in any way by these examples.

EXAMPLES

Example 1

Preparation of Polyurea-Based Capsules According to the Invention (A)

TABLE 1

Composition of capsules A according to the invention

| Ingredient | Percentage |
| --- | --- |
| Perfume Oil [1] | 27.9 |
| Uvinul A Plus [2] | 1.5 |
| Takenate ® D-110N [3] | 3.7 |
| Guanazole | 1.1 |
| Water | 38.4 |
| Gum Arabic | 0.7 |
| 3 wt % Cationic Polymer Solution [4] | 26.7 |

[1] Perfuming composition described in Table 2.
[2] Tracer for the quantification of oil deposition
[3] trimethylol propane adduct of xylylene diisocyanate; origin: Mitsui Chemicals, 75% polyisocyanate/25% ethyl acetate
[4] Salcare ® SC60 (acrylamidopropyltrimonium chloride/acrylamide copolymer; origin BASF)

TABLE 2

Perfume oil composition

| Ingredient | Parts |
| --- | --- |
| Isopropyl myristate | 0.3 |
| (2)-3-hexen-1-ol butyrate | 0.6 |
| Delta damascone | 1.0 |
| 2,4-Dimethyl-3-cyclohexene-1-carbaldehyde | 1.0 |
| Habanolide ® [1] | 3.0 |
| Hedione ® [2] | 5.0 |
| Hexyl cinnamic aldehyde | 12.0 |
| Iso E Super ® [3] | 16.0 |
| Verdyl acetate | 24.0 |
| Lilial ® [4] | 37.0 |

[1] Trademark from Firmenich; pentadecenolide, origin: Firmenich SA, Geneva, Switzerland
[2] Trademark from Firmenich; Methyl-cis-3-oxo-2-pentyl-1-cyclopentane acetate, origin: Firmenich SA, Geneva, Switzerland
[3] Trademark from IFF; 7-acetyl,1,2,3,4,5,6,7,8-octahydro-1,1,6,7-tetramethyl naphthalene
[4] Trademark from Givaudan; 3-(4-tert-butylphenyl)-2-methylpropanal General Protocol for Capsule Synthesis:

At least one polyisocyanate (e.g. Takenate® D-110N) was dissolved in a perfume oil (with Uvinul A Plus). The oil phase was then added to a biopolymer aqueous solution (e.g. 2% gum Arabic aqueous solution) and homogenized for 4 min using an Ultra-Turrax T25 disperser at 24000 rpm to form an O/W emulsion. The emulsion was pH adjusted to 10 using NaOH solution (counted as the aqueous phase). This emulsion was then stirred at 500 rpm using a mechanical overhead stirrer and optionally a reactant (e.g. a guanazole solution) was slowly added over 1 hour. Once the addition was complete, the reaction temperature was gradually elevated to 70° C. over 1 h and was maintained at 70° C. for 2 h before being allowed to cool to room temperature.

After 1.5 hours at 70° C., a cationic polymer solution was slowly added over 30 min. The reaction was then stirred for an additional 30 min at 70° C. before being allowed to cool to room temperature.

Example 2

Preparation of Polyurea-Based Capsules According to the Invention (B)

Similar protocol as described in Example 1 was applied to prepare microcapsules with a composition as reported in Table 3 below. Guanidine carbonate was used as reactant.

TABLE 3

Composition of capsules B

| Ingredient | Percentage |
|---|---|
| Perfume Oil [1] | 27.9 |
| Uvinul A Plus [2] | 1.5 |
| Takenate ® D-110N [3] | 3.7 |
| Guanidine Carbonate | 0.5 |
| Water | 39 |
| Gum Arabic | 0.7 |
| 3 wt % Polymer Solution [4] | 26.7 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Salcare ® SC60 (acrylamidopropyltrimonium chloride/acrylamide copolymer; origin BASF)

Example 3

Preparation of Polyurea-Based Capsules According to the Invention (C)

Similar protocol as described in Example 1 was applied to prepare microcapsules with a composition as reported in Table 4 below. Interfacial polymerization happened in absence of a reactant. DABCO (catalyst) was added before heating the emulsion.

TABLE 4

Composition of capsules C

| Ingredient | Percentage |
|---|---|
| Perfume Oil [1] | 27.9 |
| Uvinul A Plus [2] | 1.5 |
| Takenate ® D-110N [3] | 3.7 |
| DABCO | 0.07 |
| Water | 39.4 |
| Gum Arabic | 0.7 |
| 3 wt % Cationic Polymer Solution [4] | 26.7 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Salcare ® SC60 (acrylamidopropyltrimonium chloride/acrylamide copolymer; origin BASF)

Example 4

Preparation of Polyurethane-Based Capsules According to the Invention (D)

Similar protocol as described in Example 1 was applied to prepare microcapsules with a composition as reported in Table 5 below. Glycerol was used as reactant in conjunction with the DABCO catalyst.

TABLE 5

Composition of capsules D

| Ingredient | Percentage |
|---|---|
| Perfume Oil [1] | 27.9 |
| Uvinul A Plus [2] | 1.5 |
| Takenate ® D-110N [3] | 3.7 |
| Glycerol | 1.1 |
| DABCO | 0.07 |
| Water | 38.3 |
| Gum Arabic | 0.7 |
| 3 wt % Cationic Polymer Solution [4] | 26.7 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Salcare ® SC60 (acrylamidopropyltrimonium chloride/acrylamide copolymer; origin BASF)

Example 5

Preparation of Polyurea-Based Capsules According to the Invention (E)

Similar protocol as described in Example 1 was applied to prepare microcapsules with a composition as reported in Table 6 below. No reactant, crosslinker or catalyst was added from the aqueous phase. A cationic quaternized polymer solution was added to the slurry following the synthesis.

TABLE 6

Composition of capsules E

| Ingredient | Percentage |
|---|---|
| Perfume Oil [1] | 27.9 |
| Uvinul A Plus [2] | 1.5 |
| Takenate ® D-110N [3] | 3.7 |
| Water | 39.5 |
| Gum Arabic | 0.7 |
| 3 wt % Polymer Solution [4] | 26.7 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Salcare ® SC60 (acrylamidopropyltrimonium chloride/acrylamide copolymer; origin BASF)

Example 6

Preparation of Polyurea-Based Capsules According to the Invention (F)

Similar protocol as described in Example 1 was applied to prepare microcapsules with a composition as reported in Table 7 below. Guanidine carbonate was used as reactant. Sodium Caseinate was used as the biopolymer.

TABLE 7

Composition of capsules F

| Ingredient | Percentage |
|---|---|
| Perfume Oil [1] | 27.9 |
| Uvinul A Plus [2] | 1.5 |
| Takenate ® D-110N [3] | 3.7 |
| Guanidine Carbonate | 0.5 |
| Water | 39 |

TABLE 7-continued

Composition of capsules F

| Ingredient | Percentage |
|---|---|
| Sodium Caseinate | 0.7 |
| 3 wt % Cationic Polymer Solution [4] | 26.7 |

[1] tracer for the quantification of Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Salcare® SC60 (acrylamidopropyltrimonium chloride/acrylamide copolymer; origin BASF)

Example 7

Preparation of Polyurea-Based Capsules According to the Invention (G)

Similar protocol as described in Example 1 was applied to prepare microcapsules with a composition as reported in Table 8 below. Guanidine carbonate was used as reactant. Soy Protein was used as the biopolymer emulsifier.

TABLE 8

Composition of Capsules (G) According to the Invention

| Ingredient | Percentage |
|---|---|
| Perfume Oil [1] | 27.9 |
| Uvinul A Plus [2] | 1.5 |
| Takenate ® D-110N [3] | 3.7 |
| Guanidine Carbonate | 0.5 |
| Water | 39 |
| Soy Protein | 0.7 |
| 3 wt % Cationic Polymer Solution [4] | 26.7 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Salcare® SC60 (acrylamidopropyltrimonium chloride/acrylamide copolymer; origin BASF)

Example 8

Preparation of Polyurea-Based Capsules According to the Invention (H)

Similar protocol as described in Example 1 was applied to prepare microcapsules with a composition as reported in Table 9 below. Guanidine carbonate was used as reactant. And Gelatin Type B was used as the biopolymer.

TABLE 9

Composition of Capsules (H) According to the Invention

| Ingredient | Percentage |
|---|---|
| Perfume Oil [1] | 27.9 |
| Uvinul A Plus [2] | 1.5 |
| Takenate ® D-110N [3] | 3.7 |
| Guanidine Carbonate | 0.5 |
| Water | 39 |
| Gelatin Type B | 0.7 |
| 3 wt % Cationic Polymer Solution [4] | 26.7 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Salcare® SC60 (acrylamidopropyltrimonium chloride/acrylamide copolymer; origin BASF)

Example 9

Preparation of Silicified Inorganic/Organic Hybrid Biopolymer Capsules According to the Invention (Capsule I, Capsule J, Capsule K, Capsule L)

Similar protocol as described in Example 1 was applied to prepare microcapsules with a composition as reported in Table 10 below. The polyisocyanate concentration was systematically decreased and replaced with increasing amounts of tetraethoxysilane in the oil phase to form Capsules I, J and K. Guanidine carbonate was used as reactant for Capsule I, Capsule J and Capsule K to form a hybrid silicified polyurea-urethane. Gum Arabic was used as the biopolymer for the series. 1 wt % of cationic polymer (Salcare® SC 60) was added to the silicified capsule slurry.

Additionally, hybrid inorganic-organic Capsules L were made by introducing silanes from the aqueous phase to apply silane precipitates to the outer surface of the polyurea shell. The oil phase was prepared by mixing 5.1 g of Takenate into 40.0 g of fragrance oil (with 5 wt % Uvinul A+ tracer) and the water phase was prepared by mixing 1.0 g of Gum Arabic emulsifier into 44.9 g of 18.2MΩ-cm DI water, and adjusting the pH to 2.0. The oil phase was added to the water phase by pipette while being homogenized at 18000 rpm with a homogenizer wand. The emulsion was transferred to a jacketed reactor and set to stir at 400 rpm by overhead stirrer. A combination of silanes (including methyltriethoxysilane, tetraethoxysilane and dimethyldiethoxysilane) was then sequentially added to the reactor slowly by micropipette over the course of 15 minutes, and the reaction was allowed to stir for 1 hour before slowly ramping up the pH to 6.0 with 1400 μL of 50 wt % NaOH solution. The temperature of the jacketed reactor was increased to 70° C. for 4 hours. The slurry was then allowed to return to room temperature and stirred for another 24 hours before being drained from the reactor. An inorganic shell coating was successfully grown onto the organic capsule surface as confirmed by SEM-EDS elemental analysis and imaging. 1 wt % of cationic polymer (Salcare® SC 60) was added to the silicified capsule slurry.

TABLE 10

Composition of Capsules (I, J, K) According to the Invention

| Phase | Ingredient | Capsule I % | Capsule J % | Capsule K % |
|---|---|---|---|---|
| Oil Phase | Perfume Oil [1] | 38.0 | 38.0 | 38.0 |
|  | Uvinul A Plus [2] | 2.0 | 2.0 | 2.0 |
|  | Takenate ® D-110N [3] | 4.1 | 2.6 | 1.0 |
|  | Tetraethoxysilane (TEOS) | 1.0 | 2.6 | 4.0 |
| Water Phase | DI Water | 53.3 | 53.5 | 53.9 |
|  | Gum Arabic | 1.0 | 1.0 | 1.0 |
|  | Guanidine Carbonate | 0.6 | 0.4 | 0.1 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate

Example 10

Preparation of Control Capsules

For purpose of comparison, the following control capsules were prepared:

Capsules X with PVOH Polyvinyl Alcohol as Emulsifier (Instead of a Biopolymer) and No Cationic Polymer

TABLE 11

Composition of capsules X (control X)

| Ingredient | Percentage |
| --- | --- |
| Perfume Oil [1] | 38.0 |
| Uvinul A Plus [2] | 2.0 |
| Takenate ® D-110N [3] | 5.1 |
| Guanidine Carbonate | 0.7 |
| Water | 5.0 |
| 2 wt % PVOH Aqueous Solution | 49.2 |
| Cationic Polymer | 0.0 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate Capsules Y with PVOH Polyvinyl Alcohol as Emulsifier and a Cationic Polymer

TABLE 12

Composition of capsules Y (control Y)

| Ingredient | Percentage |
| --- | --- |
| Perfume Oil [1] | 27.9 |
| Uvinul A Plus [2] | 1.5 |
| Takenate ® D-110N [3] | 3.7 |
| Guanidine Carbonate | 0.5 |
| Water | 39 |
| PVOH | 0.7 |
| 3 wt % Cationic Polymer Solution [4] | 26.7 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Salcare ® SC60 (acrylamidopropyltrimonium chloride/acrylamide copolymer; origin BASF)

Capsules Z with Gum Arabic as Emulsifier and No Cationic Polymer

TABLE 13

Composition of capsules Z (control Z)

| Ingredient | Percentage |
| --- | --- |
| Perfume Oil [1] | 38.0 |
| Uvinul A Plus [2] | 2.0 |
| Takenate ® D-110N [3] | 5.1 |
| Guanidine Carbonate | 0.7 |
| Water | 5.0 |
| 2 wt % Gum Arabic Aqueous Solution | 49.2 |
| Cationic Polymer | 0.0 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate

Example 11

Capsules Characterization and Deposition Results
Microscopy of Capsules.

To image the microcapsules, dilute capsule slurries were dried onto carbon tape, which was adhered to aluminium stubs and then sputter coated. The stubs were placed into a scanning electron microscope (JEOL 6010 PLUS LA) for analysis. Images of Capsule B, Capsule F, and Capsule G are shown in FIG. 1 to illustrate that stable microcapsules can be made using different biomacromolecule emulsifiers.

Deposition Testing:

For the quantification of deposition, the following procedure was used. A 500 mg mini brown Caucasian hair swatch was wet with 40 mL of tap water (39° C.) aimed at the mount with a 140 mL syringe. The excess water was gently squeezed out once and 0.1 mL of a model surfactant mixture containing microcapsules loaded with a UV tracer (Uvinul A Plus) was applied with a 100 µL positive displacement pipet. The surfactant mixture was distributed with 10 horizontal and 10 vertical passes. The swatch was then rinsed with 100 mL of tap water (39° C.) with 50 mL applied to each side of the swatch aimed at the mount. The excess water was gently squeezed out and the hair swatch was then cut into a pre-weighed 20 mL scintillation vial. This process was repeated in triplicate and then the vials containing the cut hair were dried in a vacuum oven at 50-60° C. (100 Torr) for at least 5 hours. After the drying process, the vials were again weighed to determine the mass of the hair in the vials. Controls were also prepared by adding 0.1 mL of a model surfactant mixture containing microcapsules to an empty vial. 4 mL of 200 proof ethanol were then added to each vial and they were subjected to 60 min of sonication. After sonication, the samples were filtered through a 0.45 m PTFE filter and analysed with a HPLC using a UV detector. To determine the percentage of deposition of microcapsules from a model surfactant mixture, the amount of Uvinul extracted from the hair samples was compared to the amount of Uvinul extracted from the control samples.

TABLE 14

Model Surfactant Mixture

| Ingredient | Actives Percentage |
| --- | --- |
| Sodium Laurel Ether Sulfate (SLES) | 12 |
| Cocamidopropyl Betaine (CAPB) | 3 |
| Salcare ® SC 60 [1] Polymer | 0.5 |
| Water | 84 |
| Microcapsule Slurry (Equivalent Oil) | 0.5 |
| pH Adjustment (Citric Acid to pH 5.5) | *** |

[1] acrylamidopropyltrimonium chloride/acrylamide copolymer; origin BASF

Deposition onto hair swatches was measured from this simplified model surfactant mixture which is meant to be representative of personal cleansing formulations such as shampoo or shower gel. The quantitative deposition values are given in Table 15.

Figure 2:
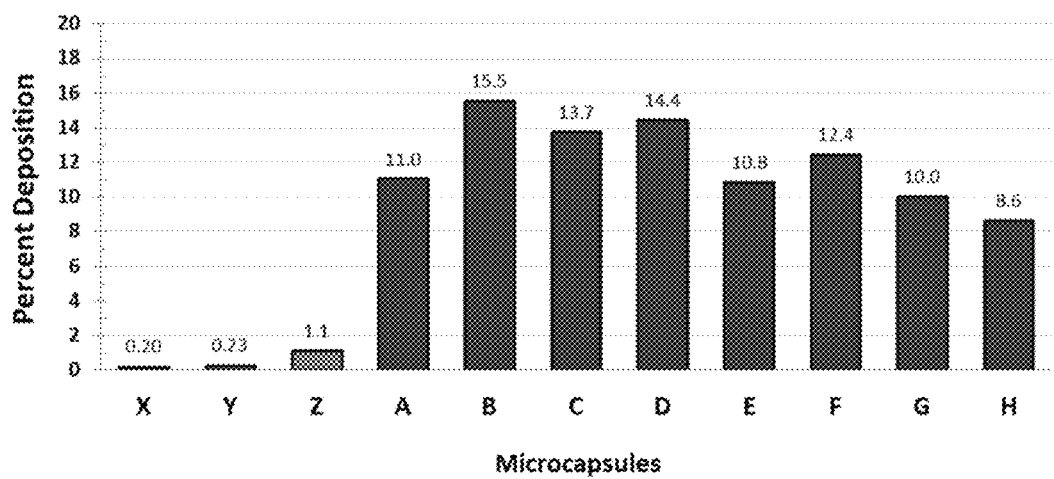
FIG. 2: Percentage of deposition of microcapsules according to the invention compared with control capsules onto hair from a model surfactant system.

The deposition results from the model surfactant system (Table 14) are shown in FIG. 2.

TABLE 15

Deposition of Control Capsules (X, Y, Z) and Capsules (A-H) onto Hair from a Model Surfactant System

| Microcapsules Sample | Percent Deposition |
| --- | --- |
| X | 0.20 |
| Y | 0.23 |
| Z | 1.1 |
| A | 11.0 |
| B | 15.5 |
| C | 13.7 |
| D | 14.4 |

TABLE 15-continued

Deposition of Control Capsules (X, Y, Z) and Capsules (A-H) onto Hair from a Model Surfactant System

| Microcapsules Sample | Percent Deposition |
|---|---|
| E | 10.8 |
| F | 12.4 |
| G | 10.0 |
| H | 8.6 |

These data illustrated in FIG. 2 demonstrate that while the addition of a cationic polymer to a neutral polyvinyl alcohol (PVOH) capsule increases the deposition onto hair swatches from 0.2% to 0.23%, the capsules according to the invention are boosting deposition up to 67 times better than prior art capsules Y containing a promoting deposition aid.

A substantial and surprising boost in deposition is attributed to the specific combination of the biopolymer emulsifier and cationic polymer in specific ratios.

Example 12

Deposition Performance in Different Rinse-Off Bases

Capsules B according to the invention described in Example 2 were tested in different formulation bases along with Capsules A and Capsules Y (control). The capsules were suspended in the different bases 24 hours prior to deposition testing performed as described in Example 11. Capsules were loaded into the formulations at either 0.2 wt % or 0.5 wt % equivalent free oil depending on the formulation.

Results are shown in Table 16. Capsules according to the invention deposit very well onto hair swatches after rinsing off complex formulations such as hair shampoo and rinse-off conditioner.

TABLE 16

Quantitative deposition results on hair swatches for Capsules A, B and Control Capsules Y from different rinse-off formulations such as the model surfactant mixture, hair shampoo and rinse-off conditioner after rinsing.

| | Percent Deposition | | |
|---|---|---|---|
| Capsule | Model Surfactant Mixture (Table 12) | Hair Shampoo (Table 18) | Rinse-Off Conditioner (Table 19) |
| A | 11 | 5.3 | 22.6 |
| B | 15.5 | 22 | Sensory Tests Only |
| Y | 0.23 | 1.5 | 4 |

TABLE 17

Rinse off conditioner base formulation

| Ingredient | Percentage |
|---|---|
| Water | 92.5 |
| Cetyl Alcohol | 3.0 |
| Amodimethicone and Trideceth-6 | 1.2 |
| Hydroxyethylcellulose | 1.0 |
| Behentrimonium Chloride | 1.0 |

TABLE 17-continued

Rinse off conditioner base formulation

| Ingredient | Percentage |
|---|---|
| Cetyl Esters | 0.5 |
| Methylparaben | 0.3 |
| Cetearyl Alcohol | 0.2 |
| Myristyl Alcohol | 0.2 |
| Chlorhexidine Dihydrochloride | 0.05 |
| Citric Acid (20% aqueous solution) | q.s. |

TABLE 18

Hair shampoo base formulation

| Ingredient | Percentage |
|---|---|
| Water | 45 |
| Sodium Laureth Sulfate | 32 |
| Sodium Chloride (10% aqueous solution) | 15 |
| Cocamidopropyl Betaine | 3.2 |
| Disodium Cocoamphodiacetate | 2 |
| Glycerin 85% | 1 |
| Polyquaternium 10 | 0.3 |
| Glyceryl Laurate | 0.3 |
| DMDM Hydantoin | 0.2 |
| Sodium Methylparaben | 0.1 |
| Citric Acid (10% aqueous solution) | q.s. |

Example 13

Deposition Performance of Capsules as a Function of Cationic Polymer

Figure 3:
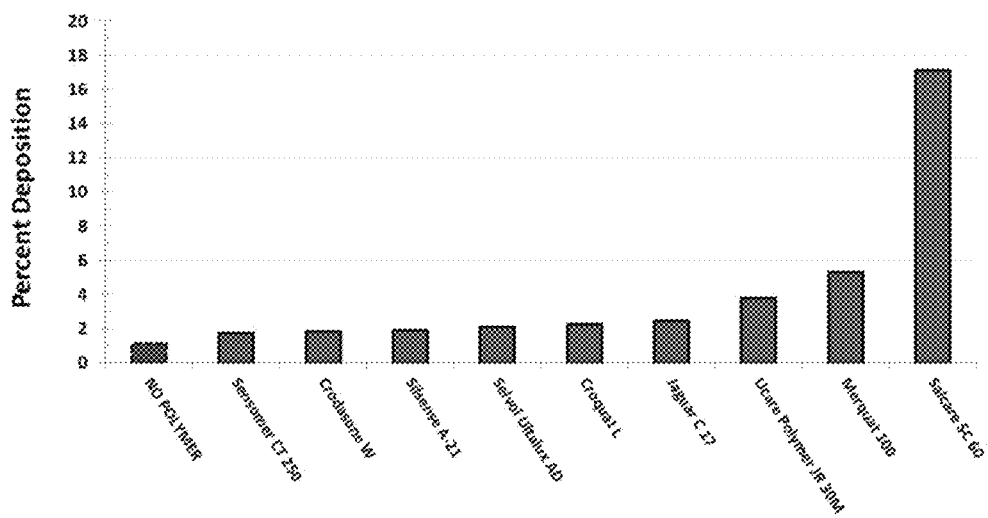
FIG. 3: Percentage of deposition from various cationic polymers used at 1 wt % in a slurry of Capsule B type microcapsules onto hair from a model surfactant mixture.

Capsules B according to the invention described in Example 2 were evaluated for deposition onto hair from a model surfactant mixture (Table 14) varying the cationic polymer selection. 1.0 wt % polymer actives from the materials listed in Table 19 were added to the Capsule B-type slurries for each respective quaternized polymer. The cationic polymer-coated capsule slurries were suspended into the model surfactant mixture 24 hours prior to deposition testing performed as described in Example 11. The results are presented in Table 19, and in FIG. 3. The strongest deposition enhancers were the cationic acrylamidopropyltrimonium chloride/acrylamide copolymer, PQ6 and PQ10 as well as the cationic guars. The control Capsule Z, without any added cationic polymer serves as the benchmark for an unmodified capsule made with a biopolymer emulsifier. The underlying biopolymer-functionalized capsule foundation interacts well with different cationic or quaternized polymers with different molecular weights and degrees of charge substitution (cationic functionality) to enhance deposition.

TABLE 19

Sampling of cationic polymers used at 1 wt % of the capsule slurry to impact deposition performance of Capsule B type microcapsules onto hair from a model surfactant mixture. The polymer-free benchmark is Capsule Z.

| Cationic Polymer INCI Name | Supplier | Supplier Tradename | % Deposition |
|---|---|---|---|
| — | — | No Polymer | 1.1 |
| Cassia Hydroxypropyltrimonium Chloride Polymer | Lubrizol | Sensomer CT 250 | 1.7 |
| Hydrolysed Wheat Protein PG-Propyl Silanetriol | Croda | Crodasone W | 1.8 |
| PEG-7 Amodimethicone | Lubrizol | Silsense A-21 | 1.9 |
| Vinyl Amine/Vinyl Alcohol Copolymer | Sekisui | Selvol Ultalux AD | 2.1 |
| Laurdimonium Hydroxypropyl Hydrolysed Collagen | Croda | Croquat L | 2.2 |
| Guar Hydroxypropyltrimonium Chloride | Rhodia | Jaguar C 17 | 2.5 |
| Polyquaternium PQ 10 | Dow | Ucare Polymer JR 30M | 3.8 |
| Polyquaternium PQ 6 | Lubrizol | Merquat 100 | 5.3 |
| acrylamidopropyltrimonium chloride/acrylamide copolymer | BASF | Salcare SC 60 | 17.1 |

Example 14

Olfactive Performance and Stability in Shampoo and Rinse-Off Conditioner
Hair Swatch Treatment and Sensory Evaluation Protocol Capsules are incorporated at the required dosage in the rinse-off base with ample stirring, and are left in the formulation at room temperature for at least 24 hours before testing. Clean, dry, 10 g hair swatches are wetted with 37° C. warm tap water for 30 seconds. 1 g of rinse-off product is applied per hair swatch, and is gently rubbed and distributed into the hair swatch evenly with gloved hands. To rinse the hair swatches, the hair swatches are double-rinsed using a sequential beaker wash involving dipping and fanning of the hair swatch in clean warm water three times per movement, followed by a 30 second rinse (15 seconds per side of the swatch) under warm running water directed at the top of the hair swatch mount (flow rate=4 L/min). The hair swatches are not squeezed dry. The sample application, distribution and rinsing are repeated a second time before placing the hair swatches on a drying rack to air dry. The hair swatches are evaluated after 24 hours by expert panelists using an intensity scale of 1-7 as follows: 1) Imperceptible; 2) Slightly Perceptible; 3) Weak; 4) Medium; 5) Sustained; 6) Intense; 7) Very Intense. Standard error bars on the figures typically denote the standard deviation of the average fragrance intensity perceived by the panelists.

Figure 4:
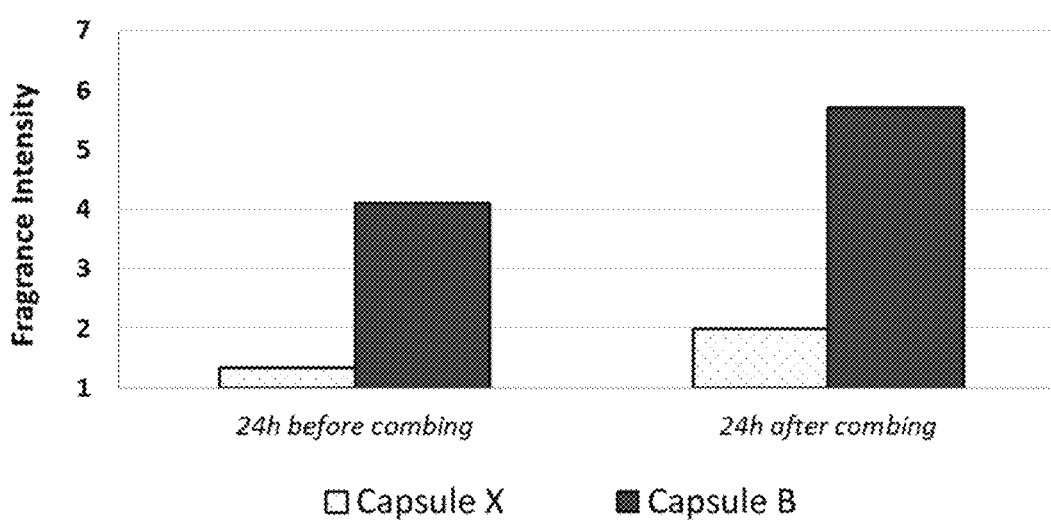
FIG. 4: Olfactive evaluation of fragrance-loaded microcapsules according to the invention (microcapsules B) compared with a control (microcapsules X) on 10 g hair swatches after rinsing. Capsules B and Capsules X were loaded into a standard transparent shampoo base at 0.4% equivalent oil and were evaluated on dried hair swatches before and after combing.

Olfactive evaluation of capsules B (capsules B above-described wherein the deposition promoting aid is Salcare® SC 60 0.8%) is compared to the performance of the control Capsules X. Capsules were dosed into the shampoo base of composition reported in Table 18 at 0.4% equivalent free oil. The combination of a biopolymer with a cationic quaternized polymer yields a substantial olfactive boost as shown in FIG. 4. Capsule B has a significantly stronger fragrance intensity which is perceived before and after combing of the hair swatches by trained panelists (n=8). It is shown that the capsules according to the invention show compared to the control higher perfume intensity both before combing and after combing.

Capsules B provided a significant boost in fragrance intensity before and after combing compared to the control Capsules X made with polyvinyl alcohol emulsifier. The combination of biopolymer and quaternized polymer yields tenacious, highly performing delivery systems.

Figure 5:
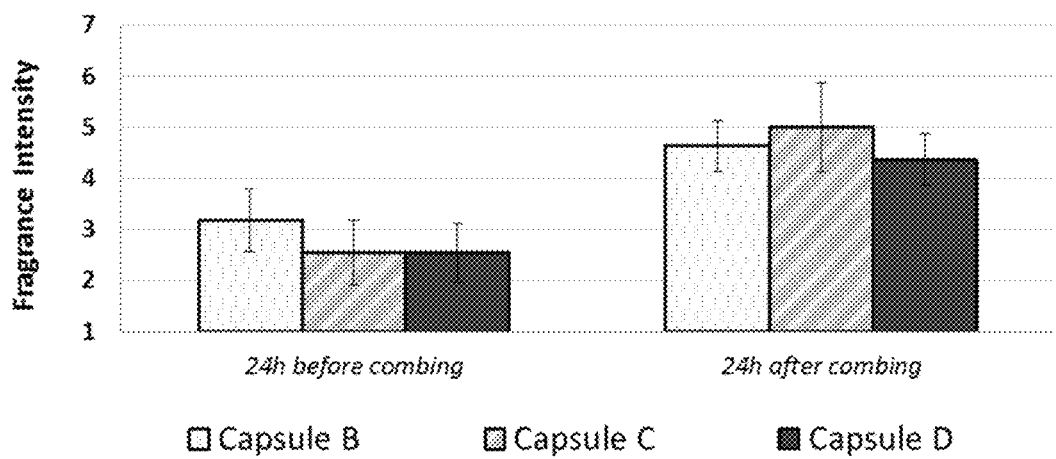
FIG. 5: Olfactive evaluation of fragrance-loaded microcapsules according to the invention (microcapsules B, C, D) on 10 g hair swatches after rinsing. Capsules were loaded into a standard transparent shampoo base at 0.2% equivalent oil, aged at 45° C. for one month and evaluated on dried hair swatches before and after combing.
Figure 6:
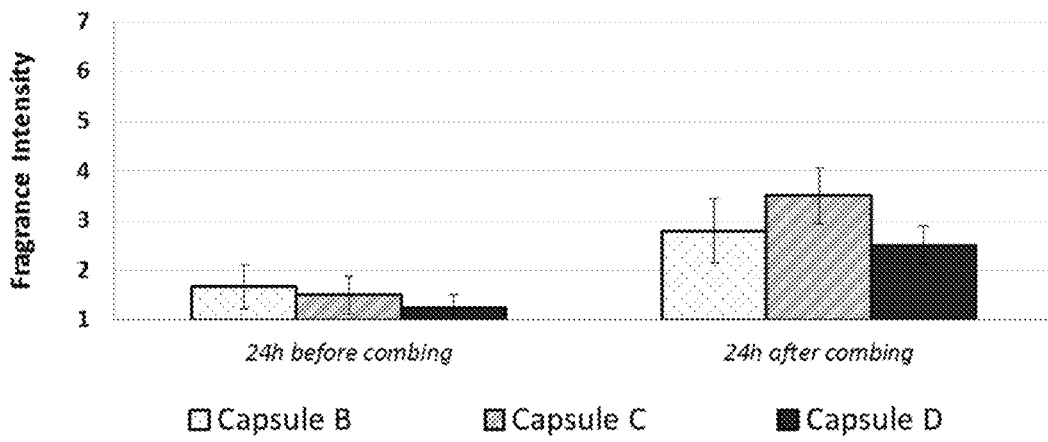
FIG. 6: Olfactive evaluation of fragrance-loaded microcapsules according to the invention (capsules B, C, D) on 10 g hair swatches after rinsing. Capsules were loaded into a rinse-off conditioner base at 0.2% equivalent oil, aged at 45° C. for one month and evaluated on dried hair swatches before and after combing.

Olfactive evaluation of capsules B (capsules B above-described wherein the deposition promoting aid is Salcare® SC 60 0.8%) was then compared to the performance of uncrosslinked polyurea-urethane Capsules C and polyurethane Capsules D in a shampoo base of composition reported in Table 18 and a rinse-off conditioner base of composition reported in Table 17. The olfactive evaluation of capsules loaded into the rinse-off formulations at 0.2% equivalent oil loading was performed by trained panelists after the samples had incubated at 45° C. for one month. This olfactive evaluation gives an indication of stability, deposition and capsule performance. Sensory evaluation of rinse-off formulations on hair swatches before and after combing provides valuable information about capsule stability (leakage or permeability of the membrane in the complex formulation), affinity (deposition and substantivity after rinsing) and activation (rupture of oil-loaded capsule when physically triggered by the combing event or friction). When the fragrance intensity delta (after combing intensity minus before combing intensity) value is examined, overall deposition and capsule performance can be assessed relative to free perfume oil, or encapsulated oil benchmark. This is especially relevant for aged samples, as high after combing fragrance intensity values indicate high affinity and activation from the rinse-off product, and confirm that the oil has remained encapsulated in the stable capsules during the stability testing. As shown in FIGS. 5 and 6, the differently-crosslinked and uncrosslinked capsules perform equally well with a strong olfactive impact after combing of the hair swatches to rupture the capsules.

Capsules were loaded into the shampoo base at 0.2% equivalent oil and were tested after 1 month at 45° C. Hair swatches were evaluated before and after combing on a 7 point fragrance intensity scale (n=10) as shown in FIG. 5.

Capsules were loaded into the rinse-off conditioner base at 0.2% equivalent oil and were tested after 1 month at 45° C. Hair swatches were evaluated before and after combing on a 7 point fragrance intensity scale (n=12) as shown in FIG. 6.

Figure 7:
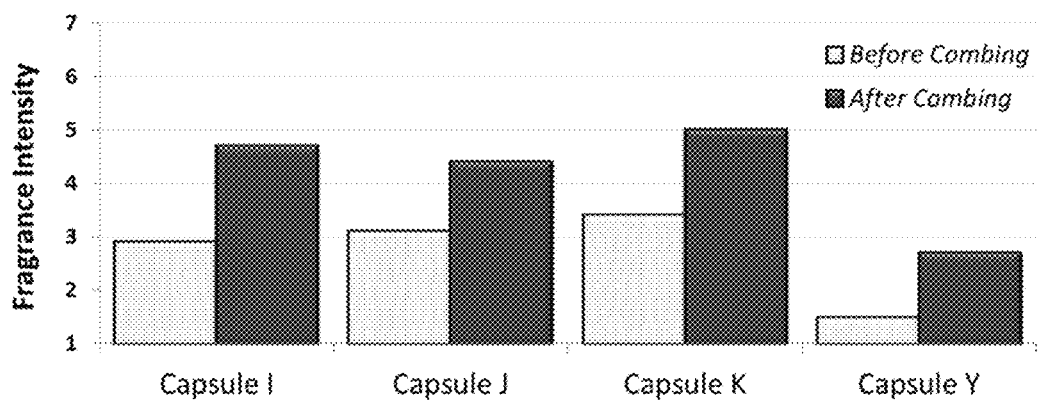
FIG. 7: Olfactive evaluation of hybrid silicified inorganic/organic microcapsules (I, J, K, and Y) from a rinse-off shampoo formulation before and after combing.

Olfactive evaluation of the inorganic/organic hybrid capsules was performed as a function of increasing silane concentration and the results are charted in FIG. 7. The deposition and olfactive performance of Capsules I, J and K following the addition of 1 wt % Salcare® SC 60 into the slurries was compared to that of Capsules Y made using polyvinyl alcohol as the emulsifier. All capsules were dosed into the shampoo with composition reported in Table 18 at 0.2% equivalent oil and were tested on 10 g hair swatches. The combination of a biopolymer with a cationic quaternized polymer yields a notable olfactive boost before and after combing as shown in FIG. 7 where the silicified hybrid capsules Capsules I, J and K are all stronger than the benchmark Capsule Y.

Capsules I, J, K, and Y were tested with 1 wt % Salcare® SC 60 polymer added to the synthesized capsule slurries and the fragrance intensities before and after combing are plotted as a function of increasing silane concentration. Silicified inorganic/organic hybrid capsules deposit and rupture significantly better than the polyvinyl alcohol-stabilized capsule benchmark.

Example 15

Figure 8:
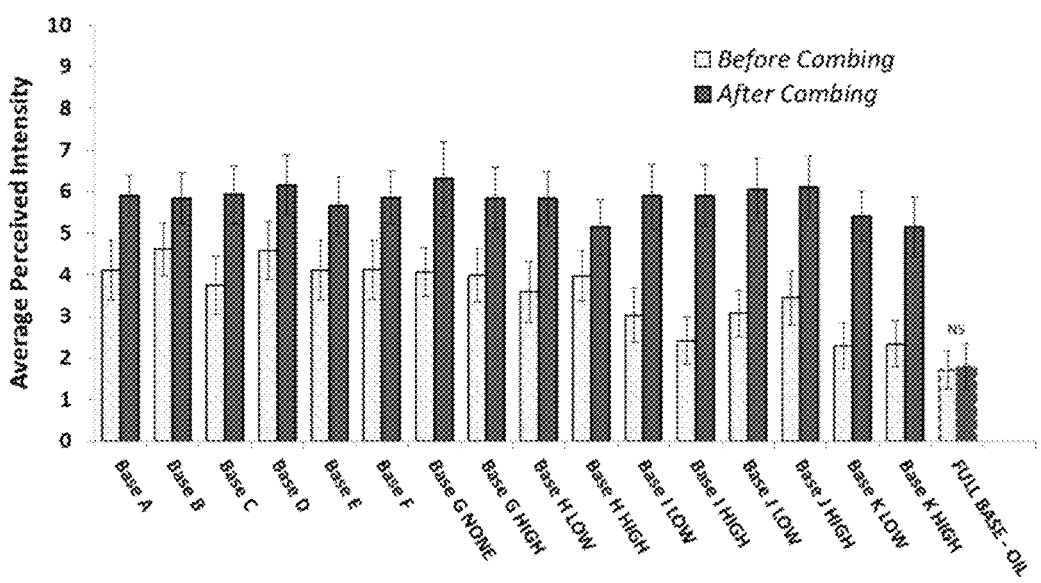
FIG. 8: Olfactive evaluation of 10 g hair swatches after washing with Capsule B loaded into several rinse-off cleanser base formulations comprising different types and loadings of surfactants, conditioners, film-formers, palliative and structuring agents.
Figure 9:
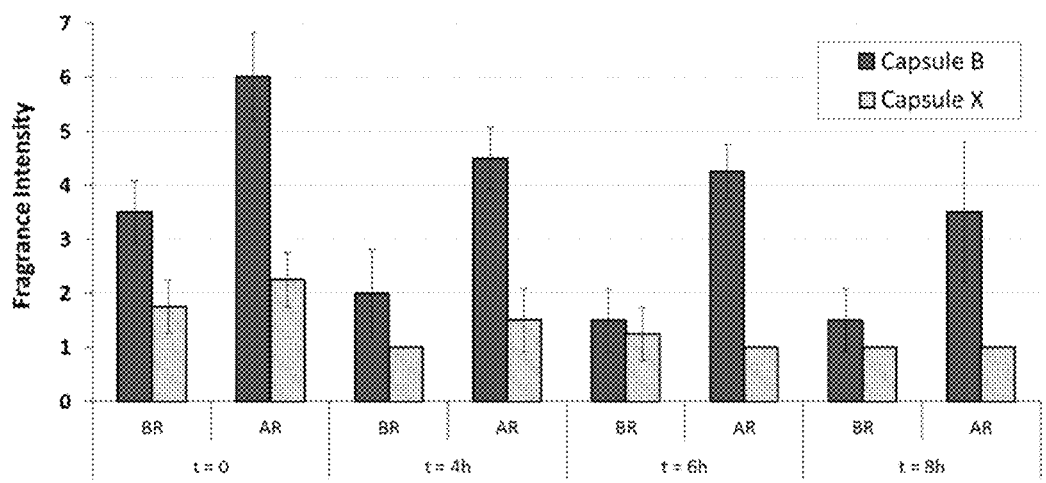
FIG. 9: Olfactive evaluation of Capsule B compared with control Capsule X on the forearm after application and rinsing of a shower gel formulation loaded with 0.325% encapsulated fragrance oil.

Olfactive Performance of Capsules in Parametrically Varied Rinse-Off Base Formulations The influence of the rinse-off base formulation on capsule deposition and performance on hair was determined using a large panel with n=29. The standard transparent hair shampoo formulation from Table 18 was parametrically modified to show that the strong deposition and activation performance of Capsules B is maintained even when the grades and loadings of the surfactants, conditioning agents and film-forming or palliative agents are varied to generate a wide range of personal cleansing formulations. The formulations are detailed in Table 20. Capsules B were loaded into the formulations at 0.2% equivalent free oil, and the 10 g hair swatches were washed, rinsed and dried for 24 hours. Panelists evaluated the fragrance intensity before and after combing the swatches with three passes of the comb, on an intensity scale of 1-10, with 10 being most intense. Additionally, free oil was loaded into the complete shampoo formulation of Table 18 and tested as a reference. The before and after combing average intensity values for the free oil sample were not determined to be statistically significant, whereas all of the formulations loaded with Capsules B had a statistically significant boost after combing. The sensory results for the evaluation of Capsules B in the 16 parametrically varied formulations of Table 20 are charted in FIG. 8. The error bars for FIG. 8 denote 95% confidence level. The capsules offer a statistically significant boost in olfactive intensity on hair swatches from all formulation variants after combing due to the high deposition and compatibility with diverse formulation ingredients, compared to hair swatches treated with free oil from the transparent hair shampoo formulation.

TABLE 20

Parametric modification of a rinse-off cleanser base formulation comprising different types and loadings of surfactants, conditioners, film-formers, palliative and structuring agents. The formulations are extensions of the standard transparent hair shampoo formulation from Table 18.

| Rinse-Off Cleanser Base Formulation | WATER | UCARE POLYMER JR-400 Poly-quaternium-10 | Hydroxyethyl-cellulose | Amodi-methicone | Quatermin 60W (Cetrimonium Chloride) | JAGUAR C-17 (Hydroxy-propyl-trimonium Chloride) | TEXAPON NSO IS (70%) Sodium Laureth Sulfate | TEGO BETAINE F50 (38%) Cocamido-propyl Betaine | AMPHOTENSID GB 2009 (39%) Disodium Cocoampho-diacetate |
|---|---|---|---|---|---|---|---|---|---|
| Base A | 82.4 | 0.1 | — | — | — | — | 12.3 | 3.2 | 2 |
| Base B | 87.3 | 0.1 | — | — | — | — | 9.6 | 2 | 1 |
| Base C | 75.0 | 0.1 | — | — | — | — | 17.4 | 4.5 | 3 |
| Base D | 76.3 | 0.1 | — | — | — | — | 19.1 | 4.5 | — |
| Base E | 77.0 | 0.1 | — | — | — | — | 19.9 | — | 3.0 |
| Base F | 66.9 | 0.1 | — | — | — | — | 23.1 | 6.0 | 4.0 |
| Base G | 82.5 | — | — | — | — | — | 12.3 | 3.2 | 2 |
| Base G high | 82.3 | 0.2 | — | — | — | — | 12.3 | 3.2 | 2 |
| Base H low | 82.0 | 0.1 | 0.4 | — | — | — | 12.3 | 3.2 | 2 |
| Base H high | 81.4 | 0.1 | 1.0 | — | — | — | 12.3 | 3.2 | 2 |
| Base I low | 80.4 | 0.1 | — | 2.0 | — | — | 12.3 | 3.2 | 2 |
| Base I high | 78.4 | 0.1 | — | 4.0 | — | — | 12.3 | 3.2 | 2 |
| Base J low | 81.4 | 0.1 | — | — | 1.0 | — | 12.3 | 3.2 | 2 |
| Base J high | 79.4 | 0.1 | — | — | 3.0 | — | 12.3 | 3.2 | 2 |
| Base K low | 82.3 | 0.1 | — | — | — | 0.1 | 12.3 | 3.2 | 2 |
| Base K high | 82.2 | 0.1 | — | — | — | 0.2 | 12.3 | 3.2 | 2 |

Example 16

Performance in Perfumed Soap Bar

Capsules B according to the invention described in Example 2 were incorporated at 3% slurry into a vegetal/palm based soap base and tested on forearms fresh after washing, and as a function of time. The sensory analysis as a function of time is given in Table 21 using the 1-7 Fragrance Intensity Scale, compared to the performance of the benchmark Capsule Z without quaternized deposition-promoting polymer. The soap base, which is typically a very challenging base for fragrance delivery systems is given in Table 22. As seen in Table 21, Capsule B provides a strong delta value (after rubbing signal minus the before rubbing signal) indicating the presence of a stable, highly-depositing fragrance microcapsules which offer long-lasting linear fragrance bursts. In contrast, no appreciable signal was detected by panelists for the control Capsule Z.

TABLE 21

Olfactive evaluation of fragrance-loaded microcapsules deposited onto the forearms of panelists from vegetal soap bars loaded with 3% capsule slurry. Intensity measurements (1-7 scale) before and after rubbing demonstrate the stability, deposition and tenacity of Capsules B compared to Capsules Z without cationic polymer, which in stark contrast, did not provide detectible signals on skin from the soap base as a function of time.

| Sample | Sensory Analysis | After wash | t = 1 hour | t = 2 hours | t = 4 hours | t = 6 hours |
|---|---|---|---|---|---|---|
| Capsule B | Before Rubbing | 3.3 | 2.3 | 1.6 | 1.4 | 1.5 |
| | After Rubbing | 4.4 | 3.6 | 3 | 2.3 | 2.2 |
| | Delta | 1.1 | 1.3 | 1.4 | 0.9 | 0.7 |

TABLE 21-continued

Olfactive evaluation of fragrance-loaded microcapsules deposited onto the forearms of panelists from vegetal soap bars loaded with 3% capsule slurry. Intensity measurements (1-7 scale) before and after rubbing demonstrate the stability, deposition and tenacity of Capsules B compared to Capsules Z without cationic polymer, which in stark contrast, did not provide detectible signals on skin from the soap base as a function of time.

| | | Time | | | | |
|---|---|---|---|---|---|---|
| Sample | Sensory Analysis | After wash | t = 1 hour | t = 2 hours | t = 4 hours | t = 6 hours |
| Capsule Z | Before Rubbing | N/A | N/A | N/A | N/A | N/A |
| | After Rubbing | N/A | N/A | N/A | N/A | N/A |
| | Delta | N/A | N/A | N/A | N/A | N/A |

TABLE 22

Vegetal/Palm Soap Base Formulation

| Ingredient | Percentage |
|---|---|
| Water | 13.0 |
| Sodium Palmate | 68.6 |
| Sodium Palm Kernelate | 17.2 |
| Tetra Sodium EDTA | 0.2 |
| Tetra Sodium Etidronate | 0.1 |
| Sodium Chloride | 0.5 |
| Glycerine | 0.5 |

Example 17

Performance of Capsules on Skin from Shower Gel

Figure 10:
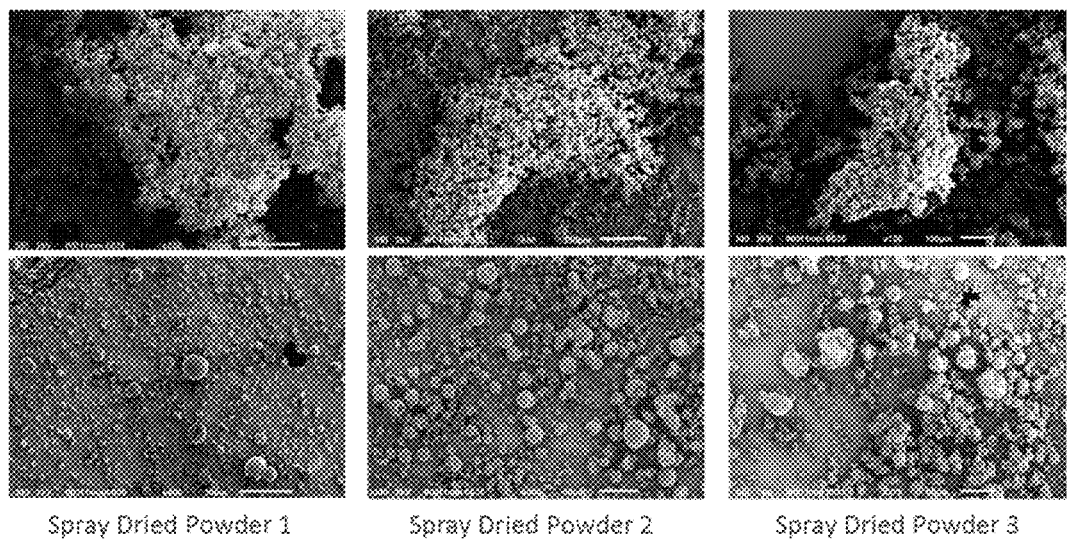
FIG. 10: Scanning electron micrographs of spray dried microcapsules (Capsules E) with three different compositions.

Capsules B according to the invention described in Example 2 were incorporated at 0.325% equivalent oil into the shower gel formulation given in Table 23 and tested on forearms after washing a designated area of skin and evaluating the fragrance intensity using the 1-7 fragrance intensity scale as a function of time, before and after rubbing the site of product application. The performance of Capsules B was benchmarked against a Capsule X made using polyvinyl alcohol. The sensory analysis as a function of time is given in FIG. 10 using the 1-7 Fragrance Intensity Scale (n=4 panelists), compared to the performance of the benchmark Capsule Z without quaternized deposition-promoting polymer.

The fragrance intensity of Capsule B, which combines a biopolymer and quaternized deposition-enhancing polymer, is significantly stronger at all time points up to 8 hours after rubbing of the forearm compared to the benchmark polyvinyl alcohol (PVOH)-stabilized microcapsules. A strong fragrance intensity signal is achieved directly after rinsing of the shower gel as well as after 8 hours after treatment of the forearm.

TABLE 23

Shower gel formulation

| Ingredient | Percentage |
|---|---|
| Water | 49.4 |
| Sodium Pareth Sulfate | 35.0 |
| Cocamidopropyl Betaine | 8.0 |
| Carbopol Aqua SF-1 Polymer | 6.0 |
| Sodium Hydroxide (20% aqueous solution) | 1.0 |
| Citric Acid (40% aqueous solution) | 0.5 |
| Methylchloroisothiazolinone | 0.1 |
| Tetrasodium EDTA | 0.1 |

Example 18

Generation of Dried Capsule Powder

A sample of uncrosslinked polyurethane type Capsules E from Example 5 were synthesized and dried to produce varied powder formulations and dual-delivery systems (encapsulated oil+free oil) using a Büchi 190 Mini Spray Dryer. The capsule slurries containing 25% oil were dried using Gum Arabic as the carrier, with and without the addition of more deposition-enhancing polymer, and finally with additional free oil which was easily stabilized by the Gum Arabic carrier. The formulations used to generate three different types of powders suitable for incorporation into various products including anhydrous bases are given in Table 24 and images of the dried powders are given in FIG. 10.

Spray dried powder 1 contains the Capsule E slurry and uses Gum Arabic as the carrier. Spray dried powder 2 additionally comprises a deposition-promoting polymer solution, and spray dried powder 3 exploits the Gum Arabic carrier to stabilize and encapsulate fragrance oil in conjunction with the pre-made capsules in order to devise a dual-release powder delivery system.

TABLE 24

Formulations for spray drying capsules in a Gum Arabic carrier. Excess deposition-promoting polymer may be added, and free oil can be easily stabilized by the Gum Arabic carrier to generate dual-release powdered delivery systems.

| | Mass (g) | | |
|---|---|---|---|
| Ingredients | Powder 1 | Powder 2 | Powder 3 |
| Capsule Slurry | 20 | 20 | 20 |
| Gum Arabic | 20 | 20 | 20 |
| 3 wt % Salcare ® SC-60[1] Polymer Solution | 0 | 10 | 10 |
| Fragrance Oil | 0 | 0 | 5 |
| Water | 100 | 100 | 100 |

[1] acrylamidopropyltrimonium chloride/acrylamide copolymer; origin BASF

Example 19

Preparation of Polyurea-Based Capsules According to the Invention (M)

Similar protocol as described in Example 1 was applied to prepare microcapsules with a composition as reported in Table 25 below. Guanidine carbonate was used as reactant. Gelatin Type A was used as the biopolymer emulsifier.

TABLE 25

Composition of Capsules (M) According to the Invention

| Ingredient | Percentage |
|---|---|
| Perfume Oil [1] | 25.3 |
| Uvinul A Plus [2] | 1.3 |
| Takenate ® D-110N [3] | 3.4 |
| Guanidine Carbonate | 0.5 |

TABLE 25-continued

Composition of Capsules (M) According to the Invention

| Ingredient | Percentage |
| --- | --- |
| Water | 35.5 |
| Gelatin (Type A) | 0.7 |
| 3 wt % Polymer Solution [4] | 33.3 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Salcare ® SC60 (acrylamidopropyltrimonium chloride/acrylamide copolymer; origin BASF)

Example 20

Preparation of Polyurea-Based Capsules According to the Invention (N)

Similar protocol as described in Example 1 was applied to prepare microcapsules with a composition as reported in Table 26 below. Guanidine carbonate was used as reactant. Bovine Serum Albumin was used as the biopolymer emulsifier.

TABLE 26

Composition of Capsules (N) According to the Invention

| Ingredient | Percentage |
| --- | --- |
| Perfume Oil [1] | 25.3 |
| Uvinul A Plus [2] | 1.3 |
| Takenate ® D-110N [3] | 3.4 |
| Guanidine Carbonate | 0.5 |
| Water | 35.5 |
| Bovine Serum Albumin | 0.7 |
| 3 wt % Polymer Solution [4] | 33.3 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Salcare ® SC60 (acrylamidopropyltrimonium chloride/acrylamide copolymer; origin BASF)

Example 21

Preparation of Polyurea-Based Capsules According to the Invention (O)

Similar protocol as described in Example 1 was applied to prepare microcapsules with a composition as reported in Table 27 below. Guanidine carbonate was used as reactant. Sugar Beet Pectin was used as the biopolymer emulsifier.

TABLE 27

Composition of Capsules (O) According to the Invention

| Ingredient | Percentage |
| --- | --- |
| Perfume Oil [1] | 25.3 |
| Uvinul A Plus [2] | 1.3 |
| Takenate ® D-110N [3] | 3.4 |
| Guanidine Carbonate | 0.5 |
| Water | 35.5 |
| Sugar Beet Pectin | 0.7 |
| 3 wt % Polymer Solution [4] | 33.3 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Salcare ® SC60 (acrylamidopropyltrimonium chloride/acrylamide copolymer; origin BASF)

Example 22

Preparation of Polyurea-Based Capsules According to the Invention (P)

Similar protocol as described in Example 1 was applied to prepare microcapsules with a composition as reported in Table 28 below. Guanidine carbonate was used as reactant. Sericin was used as the biopolymer emulsifier.

TABLE 28

Composition of Capsules (P) According to the Invention

| Ingredient | Percentage |
| --- | --- |
| Perfume Oil [1] | 25.3 |
| Uvinul A Plus [2] | 1.3 |
| Takenate ® D-110N [3] | 3.4 |
| Guanidine Carbonate | 0.5 |
| Water | 35.5 |
| Sericin [4] | 0.7 |
| 3 wt % Polymer Solution [5] | 33.3 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Purolan Sericin (INCI Name: hydrolyzed sericin; origin Lanxess)
[5] Salcare ® SC60 (acrylamidopropyltrimonium chloride/acrylamide copolymer; origin BASF)

Example 23

Preparation of Polyurea-Based Capsules According to the Invention (Q)

Similar protocol as described in Example 5 was applied to prepare microcapsules with a composition as reported in Table 29 below. No reactant, crosslinker or catalyst was added from the aqueous phase. Pseudocollagen was used as the biopolymer emulsifier.

TABLE 29

Composition of Capsules (Q) According to the Invention

| Ingredient | Percentage |
| --- | --- |
| Perfume Oil [1] | 25.3 |
| Uvinul A Plus [2] | 1.3 |
| Takenate ® D-110N [3] | 3.4 |
| Water | 36.0 |
| Pseudocollagen [4] | 0.7 |
| 3 wt % Polymer Solution [5] | 33.3 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Pseudocollagen (INCI Name: Yeast Extract; origin Lonza)
[5] Salcare ® SC60 (acrylamidopropyltrimonium chloride/acrylamide copolymer; origin BASF)

Example 24

Preparation of Polyurea-Based Capsules According to the Invention (R)

Similar protocol as described in Example 5 was applied to prepare microcapsules with a composition as reported in Table 30 below. No reactant, crosslinker or catalyst was added from the aqueous phase. Biopolymer SA-N was used as the biopolymer emulsifier.

TABLE 30

Composition of Capsules (R) According to the Invention

| Ingredient | Percentage |
| --- | --- |
| Perfume Oil [1] | 25.3 |
| Uvinul A Plus [2] | 1.3 |
| Takenate ® D-110N [3] | 3.4 |
| Water | 36.0 |
| Biopolymer SA-N [4] | 0.7 |
| 3 wt % Polymer Solution [5] | 33.3 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Biopolymer SA-N (INCI Name: Hyaluronic Acid (and) Albumen (and) Dextran Sulfate; origin Lipo Chemicals)
[5] Salcare ® SC60 (acrylamidopropyltrimonium chloride/acrylamide copolymer; origin BASF)

Example 25

Preparation of Polyurea-Based Capsules According to the Invention (S)

Similar protocol as described in Example 5 was applied to prepare microcapsules with a composition as reported in Table 31 below. No reactant, crosslinker or catalyst was added from the aqueous phase. Pentacare-NA PF was used as the biopolymer emulsifier.

TABLE 31

Composition of Capsules (S) According to the Invention

| Ingredient | Percentage |
| --- | --- |
| Perfume Oil [1] | 25.3 |
| Uvinul A Plus [2] | 1.3 |
| Takenate ® D-110N [3] | 3.4 |
| Water | 36.0 |
| Pentacare-NA PF [4] | 0.7 |
| 3 wt % Polymer Solution [5] | 33.3 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Pentacare-NA PF (INCI Name: Hydrolyzed Wheat Gluten (and) *Ceratonia Siliqua* (Carob) Gum (and) Aqua (and) Sodium Dextran Sulfate (and) Bis-Hydroxyethyl Tromethamine (and) Phenoxyethanol (and) Ethylhexylglycerin; origin DSM Nutritional Products, LLC)
[5] Salcare ® SC60 (acrylamidopropyltrimonium chloride/acrylamide copolymer; origin BASF)

Example 26

Preparation of Polyurea-Based Capsules According to the Invention (T)

Similar protocol as described in Example 5 was applied to prepare microcapsules with a composition as reported in Table 32 below. No reactant, crosslinker or catalyst was added from the aqueous phase. Hydrolyzed Soy Protein was used as the biopolymer emulsifier.

TABLE 32

Composition of Capsules (T) According to the Invention

| Ingredient | Percentage |
| --- | --- |
| Perfume Oil [1] | 25.3 |
| Uvinul A Plus [2] | 1.3 |
| Takenate ® D-110N [3] | 3.4 |
| Water | 36.0 |
| Hydrolyzed Soy Protein [4] | 0.7 |
| 3 wt % Polymer Solution [5] | 33.3 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Hydrolyzed Soy Protein (INCI Name: Hydrolyzed Soy Protein; origin Vege Tech Company)
[5] Salcare ® SC60 (acrylamidopropyltrimonium chloride/acrylamide copolymer; origin BASF)

Example 27

Preparation of Polyurea-Based Capsules According to the Invention (U)

Similar protocol as described in Example 5 was applied to prepare microcapsules with a composition as reported in Table 33 below. No reactant, crosslinker or catalyst was added from the aqueous phase. Revitalin PF was mixed 1:1 with Gum Arabic and the mixture was used as the biopolymer emulsifier.

TABLE 33

Composition of Capsules (U) According to the Invention

| Ingredient | Percentage |
| --- | --- |
| Perfume Oil [1] | 25.3 |
| Uvinul A Plus [2] | 1.3 |
| Takenate ® D-110N [3] | 3.4 |
| Water | 36.0 |
| Revitalin PF [4]/Gum Arabic | 0.7 |
| 3 wt % Polymer Solution [5] | 33.3 |

[1] Perfuming composition from Table 2
[2] tracer for the quantification of oil deposition
[3] trimethylol propane adduct of xylylene diisocyanate; origin: Mitsui Chemicals, 75% polyisocyanate/25% ethyl acetate
[4] Revitalin ® PF (INCI Name: Glycoproteins (and) Glutamic Acid (and) Valine (and) Threonine (and) Aqua (and) Phenoxyethanol (and) Ethylhexylglycerin (and) Sodium Metabisulfite; origin DSM Nutritional Products, LLC)
[5] Salcare ® SC60 (acrylamidopropyltrimonium chloride/acrylamide copolymer; origin BASF)

Example 28

Deposition of microcapsules according to the invention (M-U) onto hair swatches was measured from rinse-off shampoo (Table 18) using the protocol described in Example 11 and compared to control microcapsules X, Y, Z. Capsules were loaded into the formulation at 0.5 wt % equivalent free oil. The quantitative deposition values are given in Table 34. The combination of biopolymer emulsifier with cationic polymer yields significant improvement in deposition compared to the control microcapsules.

Figure 11:
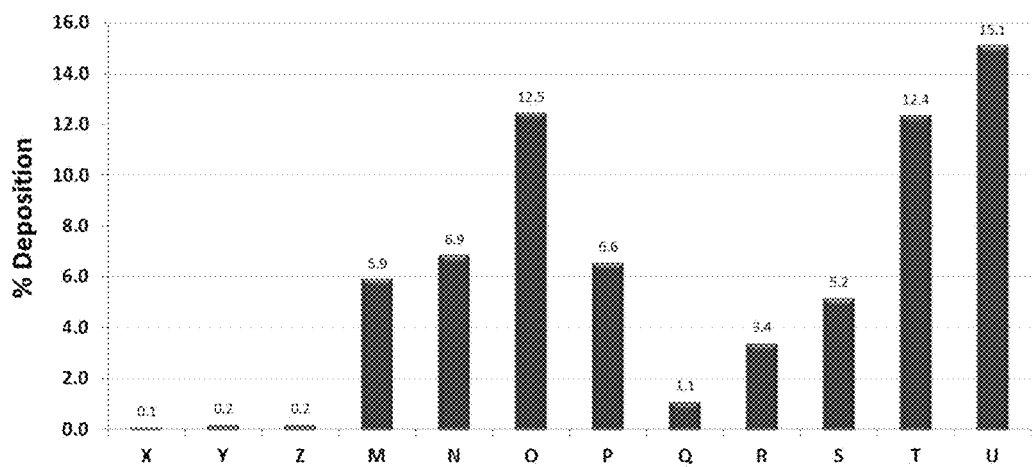
FIG. 11: Percentage of deposition of microcapsules according to the invention (microcapsules M-U) compared with control capsules (microcapsules X, Y, Z) onto hair from a standard transparent shampoo base loaded with 0.5% equivalent oil.

The deposition results from the rinse-off shampoo (Table 18) are shown in FIG. 11.

TABLE 34

Deposition of Control Capsules (X, Y, Z) and Capsules (M-U) onto Hair from a Model Surfactant System

| Microcapsules Sample | Percent Deposition |
| --- | --- |
| X | 0.12 |
| Y | 0.20 |
| Z | 0.22 |

TABLE 34-continued

Deposition of Control Capsules (X, Y, Z) and Capsules (M-U) onto Hair from a Model Surfactant System

| Microcapsules Sample | Percent Deposition |
|---|---|
| M | 5.95 |
| N | 6.89 |
| O | 12.47 |
| P | 6.60 |
| Q | 1.12 |
| R | 3.42 |
| S | 5.19 |
| T | 12.36 |
| U | 15.14 |

Example 29

Figure 12:
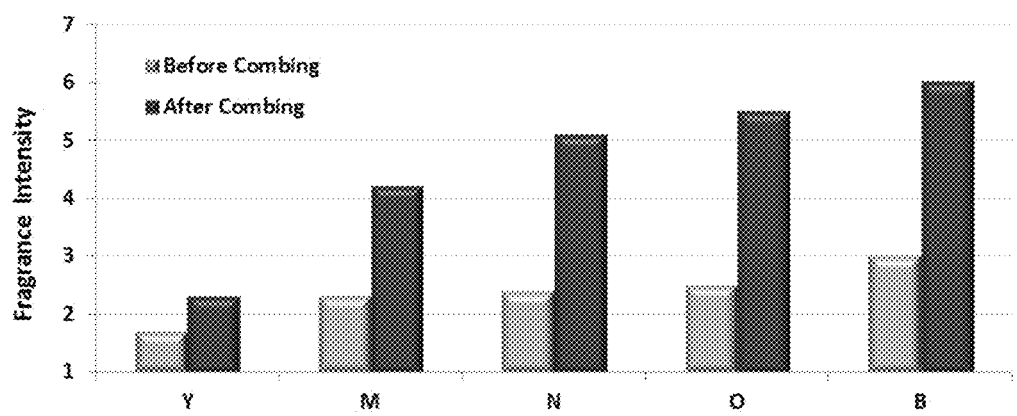
FIG. 12: Olfactive evaluation of fragrance-loaded microcapsules according to the invention (microcapsules Y, M, N, O, and B) on 10 g hair swatches after rinsing. Capsules Y, M, N, O and B were loaded into a standard transparent shampoo base at 0.2% equivalent oil and were evaluated on dried hair swatches before and after combing.

Olfactive evaluation of capsules M, N, O and B was compared to the performance of the control Capsules Y. Capsules were dosed into the shampoo base of composition reported in Table 18 at 0.2% equivalent free oil. The combination of a biopolymer with a cationic quaternized polymer yields a substantial olfactive boost as shown in FIG. 12. Capsules M, N, O and B have a significantly stronger fragrance intensity which is perceived before and after combing of the hair swatches by trained panelists (n=12). It is shown that the capsules according to the invention show higher perfume intensity both before combing and after combing compared to the controls.

Example 30

Figure 13:
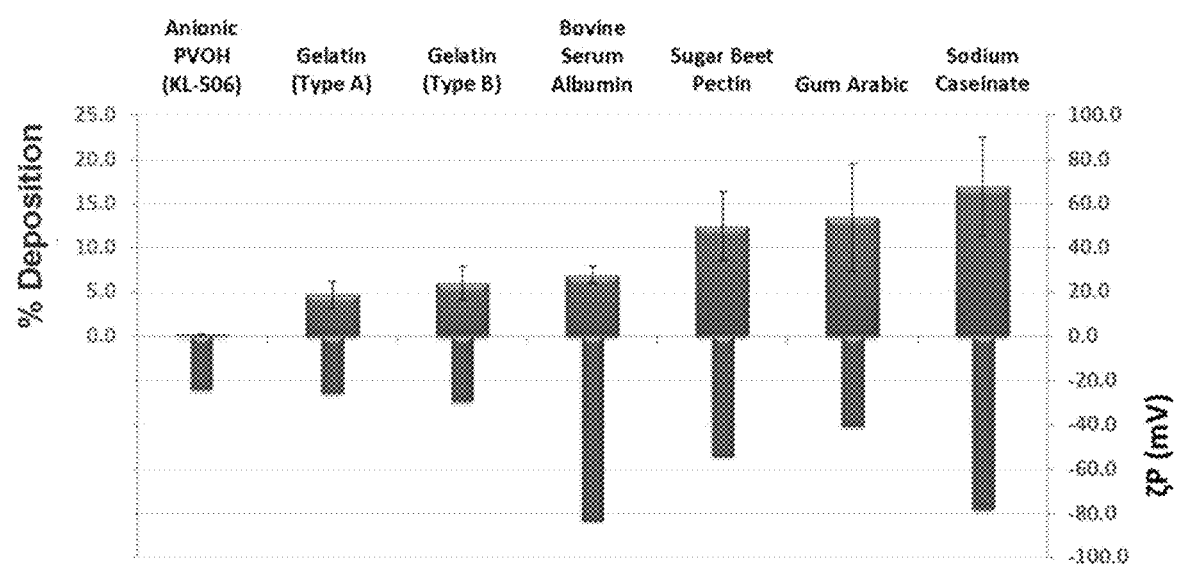
FIG. 13: Correlation between zeta potential measurements (narrow negative bars) and percentage of deposition (wide positive bars) for capsules having different compositions.

Deposition and zeta potentials of microcapsules according to the invention (M, N, O, A and F) were measured and compared to control microcapsules X. Zeta potentials were determined and reported for native capsules (prior to cationic polymer addition) in 1 mM KCL, pH 5.5 using a Malvern ZetaSizer Nano ZS-90. All capsules were determined to have nearly identical zeta potentials of +40 mV following the addition of cationic polymer Salcare SC 60 and this is not shown on the plot. Deposition was measured onto hair swatches from rinse-off shampoo (using the protocol described in Example 11) with capsules following cationic polymer addition. Capsules were loaded into the formulation at 0.5 wt % equivalent free oil. Both values of zeta potentials (mV, secondary y-axis) and percentage of capsules deposited onto hair after washing (% deposition, primary y-axis) are provided in a same graph in FIG. 13. These data underline that there is no correlation between the magnitude of zeta potential and percentage of deposition, and that judicious selection of anionic or amphoteric biopolymers with different structures and conformations in combination with cationic polymer is necessary for enhanced performance. In other words, the magnitude of zeta potential is surprisingly not the sole driver of deposition. Indeed, zeta potentials for control microcapsules X, for capsules M (Gelatin A), and for capsules H (Gelatin B) are similar, whereas the percentage of deposition for capsules M and H is at least 50 times greater than for control capsules X onto hair after rinsing.

What is claimed is:

1. A core-shell microcapsule slurry comprising at least one microcapsule, the at least one microcapsule having:
    a) an oil-based core;
    b) a polymeric shell formed by interfacial polymerization in the presence of an anionic or amphiphilic biopolymer, wherein the polymeric shell comprises urea linkages or urethane linkages; and
    c) a coating comprising a cationic polymer, wherein the cationic polymer comprises an acrylamidopropyltrimonium chloride/acrylamide copolymer;
    wherein the weight ratio between the anionic or amphiphilic biopolymer present during the formation of the polymeric shell and the cationic polymer in the core-shell microcapsule slurry is between 0.5 and 2.0, and wherein the anionic or amphiphilic biopolymer has not been modified by means of chemical derivatization to chemically graft on different functional groups with different properties.

2. The core-shell microcapsule slurry according to claim 1, wherein the anionic or amphiphilic biopolymer is selected from the group consisting of gum Arabic, soy protein, sodium caseinate, gelatin, bovine serum albumin, sugar beet pectin, hydrolyzed soy protein, hydrolyzed sericin, yeast extract collagen equivalent, a mixture of hyaluronic acid, albumen and dextran sulfate, carob gum, a mixture of gum Arabic and glycoproteins, and mixtures thereof.

3. The core-shell microcapsule slurry according to claim 1, wherein the oil comprises a perfume.

4. A microcapsule powder obtained by drying the core-shell microcapsule slurry of claim 1.

5. A process for the preparation of the core-shell microcapsule slurry of claim 1, comprising the following steps:
    a) dissolving at least one polyisocyanate having at least two isocyanate groups in an oil to form an oil phase;
    b) preparing an aqueous solution of an anionic or amphiphilic biopolymer to form a water phase;
    c) adding the oil phase to the water phase to form an oil-in-water dispersion, wherein the mean droplet size is between 1 and 500 µm;
    d) adding a polyamine or a polyol to the oil-in-water dispersion to induce interfacial polymerization and form microcapsules in the form of a slurry;
    e) adding a cationic polymer comprising an acrylamidopropyltrimonium chloride/acrylamide copolymer; and
    f) optionally drying the core-shell microcapsule slurry to obtain a microcapsule powder;
    wherein the anionic or amphiphilic biopolymer present during the formation of the polymeric shell and the cationic polymer are added in amounts such that the weight ratio between the biopolymer and the cationic polymer in the core-shell microslurry is between 0.5 and 2.0 an, d wherein the anionic or amphiphilic biopolymer has not been modified by means of chemical derivatization to chemically graft on different functional groups with different properties.

6. The process according to claim 5, wherein the oil comprises a perfume or flavor added in an amount between 20 to 50% by weight relative to the total weight of the core-shell microcapsule slurry.

7. The process according to claim 5, wherein the biopolymer is used in an amount between 0.1 and 5 wt % relative to the total weight of the core-shell microcapsule slurry.

8. The process according to claim 5, wherein the cationic polymer is used in an amount between 0.1 and 5 wt % of the core-shell microcapsule slurry.

9. A perfuming composition comprising
    (i) the core-shell microcapsule slurry of claim 3;
    (ii) at least one ingredient selected from the group consisting of a perfumery carrier and a perfuming co-ingredient; and
    (iii) optionally a perfumery adjuvant.

10. A A home-care or personal-care product comprising the core-shell microcapsule slurry of claim 3.

11. The home-care or personal-care product according to claim 10, selected from the group consisting of a shampoo, a shower gel, a rinse-off conditioner, and a soap bar.

12. A method for improving deposition of microcapsules on a surface, comprising treating the surface with the perfuming composition of claim 9.

* * * * *